(12) United States Patent
Kojima et al.

(10) Patent No.: US 7,627,082 B2
(45) Date of Patent: Dec. 1, 2009

(54) RADIOLOGICAL IMAGING APPARATUS

(75) Inventors: Shinichi Kojima, Hitachi (JP); Takashi Okazaki, Hitachinaka (JP); Yuuichirou Ueno, Hitachi (JP); Kikuo Umegaki, Hitachinaka (JP); Kensuke Amemiya, Hitachinaka (JP); Kazuhiro Takeuchi, Hitachi (JP); Hiroshi Kitaguchi, Naka-machi (JP); Kazuma Yokoi, Hitachi (JP); Norihito Yanagita, Hitachi (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 11/907,115

(22) Filed: Oct. 9, 2007

(65) Prior Publication Data
US 2008/0137804 A1    Jun. 12, 2008

Related U.S. Application Data

(63) Continuation of application No. 10/270,151, filed on Oct. 15, 2002, now Pat. No. 7,297,958.

(30) Foreign Application Priority Data

Dec. 3, 2001   (JP)   ............................. 2001-368062
Mar. 5, 2002   (JP)   ............................. 2002-059414

(51) Int. Cl.
    *A61B 6/00*   (2006.01)
(52) U.S. Cl. ..................... 378/19; 378/63; 250/363.04
(58) Field of Classification Search .............. 378/4–20, 378/63, 98.8; 250/251, 252.1, 367, 370.1, 250/370.06–370.13, 363.02–363.05, 363.09, 250/366, 368; 600/407, 425, 427
    See application file for complete search history.

(56) References Cited

U.S. PATENT DOCUMENTS 4,247,774  A    1/1981    Brooks
(Continued)

FOREIGN PATENT DOCUMENTS

JP    61-51585    3/1986
(Continued)

OTHER PUBLICATIONS

Japanese-language Office Action with English-language Translation dated Mar. 29, 2005.
(Continued)

*Primary Examiner*—Courtney Thomas
(74) *Attorney, Agent, or Firm*—Dickstein Shapiro LLP

(57) ABSTRACT

A radiological imaging apparatus of the present invention comprises an image pickup device and a medical examinee holding device that is provided with a bed. The image pickup device includes a large number of radiation detectors and radiation detector support plates. A large number of radiation detectors are mounted around the circumference of a through-hole and arranged in the axial direction of the through-hole. The radiation detectors are arranged in three layers formed radically with respect to the center of the through-hole and mounted on the lateral surfaces of the radiation detector support plates. Since the radiation detectors are not only arranged in the axial direction and circumferential direction of the through-hole but also arrayed in the radial direction, it is possible to obtain accurate information about a γ-ray arrival position in the radial direction of the through-hole (the positional information about a radiation detector from which a γ-ray image pickup signal is output). The use of accurate information about γ-ray arrival increases the tomogram accuracy. As a result, the present invention enhances the tomogram accuracy, that is, the PET examination accuracy.

11 Claims, 16 Drawing Sheets

U.S. PATENT DOCUMENTS

| | | | |
|---|---|---|---|
| 4,511,799 A | 4/1985 | Bjorkholm |
| 4,677,299 A | 6/1987 | Wong |
| 4,709,382 A | 11/1987 | Sones |
| 4,792,900 A | 12/1988 | Sones et al. |
| 4,857,737 A | 8/1989 | Kamae et al. |
| 4,870,667 A | 9/1989 | Brunnett et al. |
| 4,891,833 A | 1/1990 | Bernardi |
| 5,241,181 A | 8/1993 | Mertens et al. |
| 5,272,343 A | 12/1993 | Stearns |
| 5,424,946 A | 6/1995 | Stearns |
| 5,567,944 A | 10/1996 | Rohe et al. |
| 5,585,637 A | 12/1996 | Bertelsen et al. |
| 5,753,917 A | 5/1998 | Engdahl |
| 5,786,597 A | 7/1998 | Lingren et al. |
| 5,793,045 A | 8/1998 | DiFilippo et al. |
| 5,821,540 A | 10/1998 | Sato et al. |
| 5,821,541 A | 10/1998 | Tumer |
| 5,841,140 A | 11/1998 | McCroskey et al. |
| 6,121,619 A | 9/2000 | Johnsen et al. |
| 6,232,604 B1 | 5/2001 | McDaniel et al. |
| 6,246,706 B1 | 6/2001 | Kafka et al. |
| 6,249,003 B1 | 6/2001 | Culp |
| 6,255,657 B1 | 7/2001 | Cole et al. |
| 6,285,740 B1 | 9/2001 | Seely et al. |
| 6,326,624 B1 | 12/2001 | Chapuis et al. |
| 6,346,706 B1 | 2/2002 | Rogers et al. |
| 6,377,838 B1 | 4/2002 | Iwanczyk et al. |
| 6,448,559 B1 | 9/2002 | Saoudi et al. |
| 6,449,331 B1 | 9/2002 | Nutt et al. |
| 6,484,051 B1 | 11/2002 | Daniel |
| 6,490,476 B1 | 12/2002 | Townsend et al. |
| 6,528,793 B1 | 3/2003 | Chen et al. |
| 6,528,795 B2 | 3/2003 | Kurfess |
| 6,590,213 B2 | 7/2003 | Wollenweber |
| 6,670,614 B1 | 12/2003 | Plut et al. |
| 2002/0090050 A1 | 7/2002 | Nutt et al. |
| 2003/0075685 A1 | 4/2003 | Yamakawa |

FOREIGN PATENT DOCUMENTS

| | | |
|---|---|---|
| JP | 61-226674 | 10/1986 |
| JP | 62-52479 | 3/1987 |
| JP | 63-158490 | 7/1988 |
| JP | A 2-17488 | 1/1990 |
| JP | A-3-46884 | 2/1991 |
| JP | 3-46884 | 4/1991 |
| JP | 5-302979 | 11/1993 |
| JP | A-6-51069 | 2/1994 |
| JP | A 6-324158 | 11/1994 |
| JP | A 7-140253 | 6/1995 |
| JP | A 8-75862 | 3/1996 |
| JP | 8-122438 | 5/1996 |
| JP | A-8-160147 | 6/1996 |
| JP | 9-005441 | 1/1997 |
| JP | 11-344568 | 12/1999 |
| JP | A-2000-56021 | 2/2000 |
| JP | 2000-075034 | 3/2000 |
| JP | 2001-330673 | 11/2001 |

OTHER PUBLICATIONS

Japanese-language Office Action with English-language Translation dated Aug. 30, 2005.

Japanese-language Decision of Rejection with English-language Translation dated Jan. 17, 2006.

Japanese-language Dismissal of Amendment with English-language Translation dated Jan. 17, 2006.

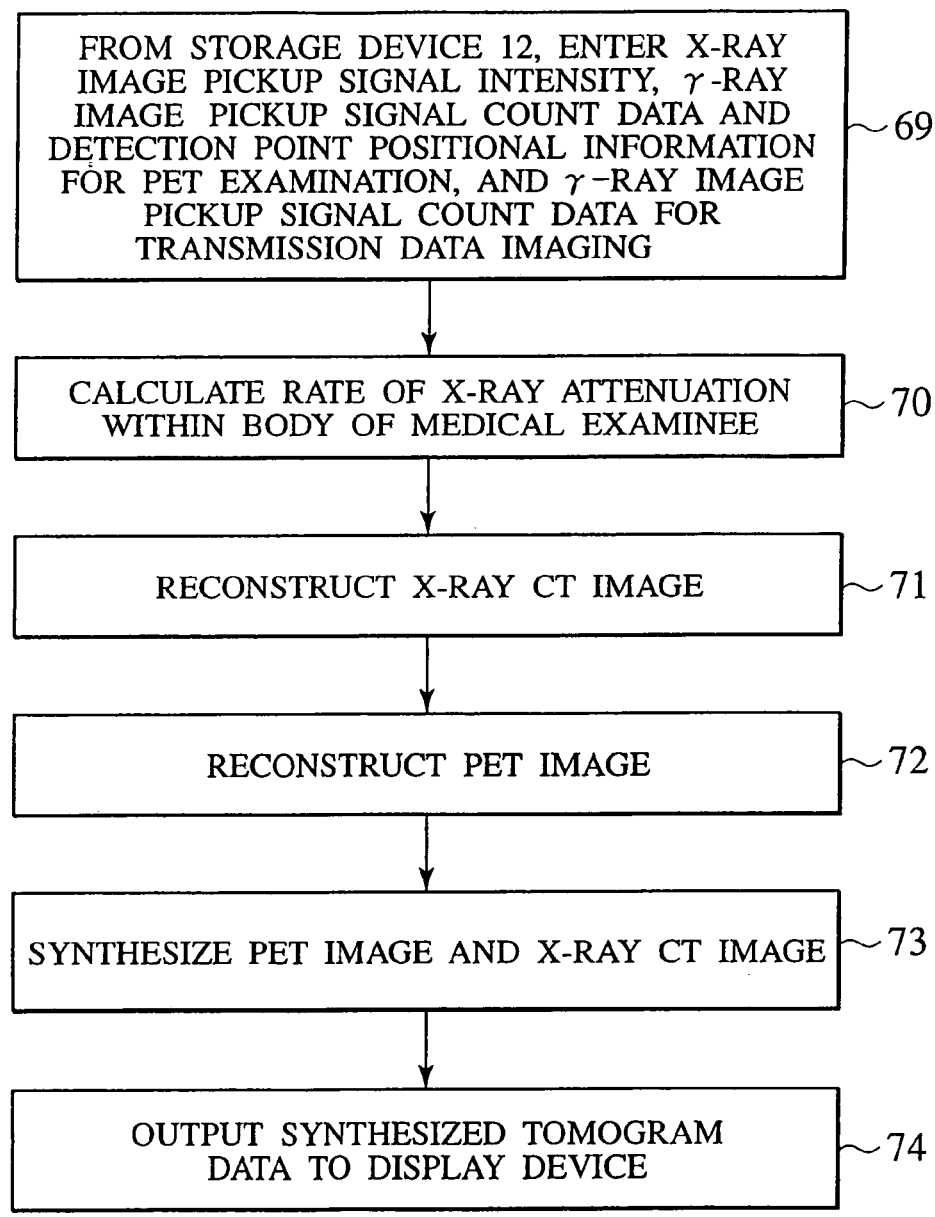

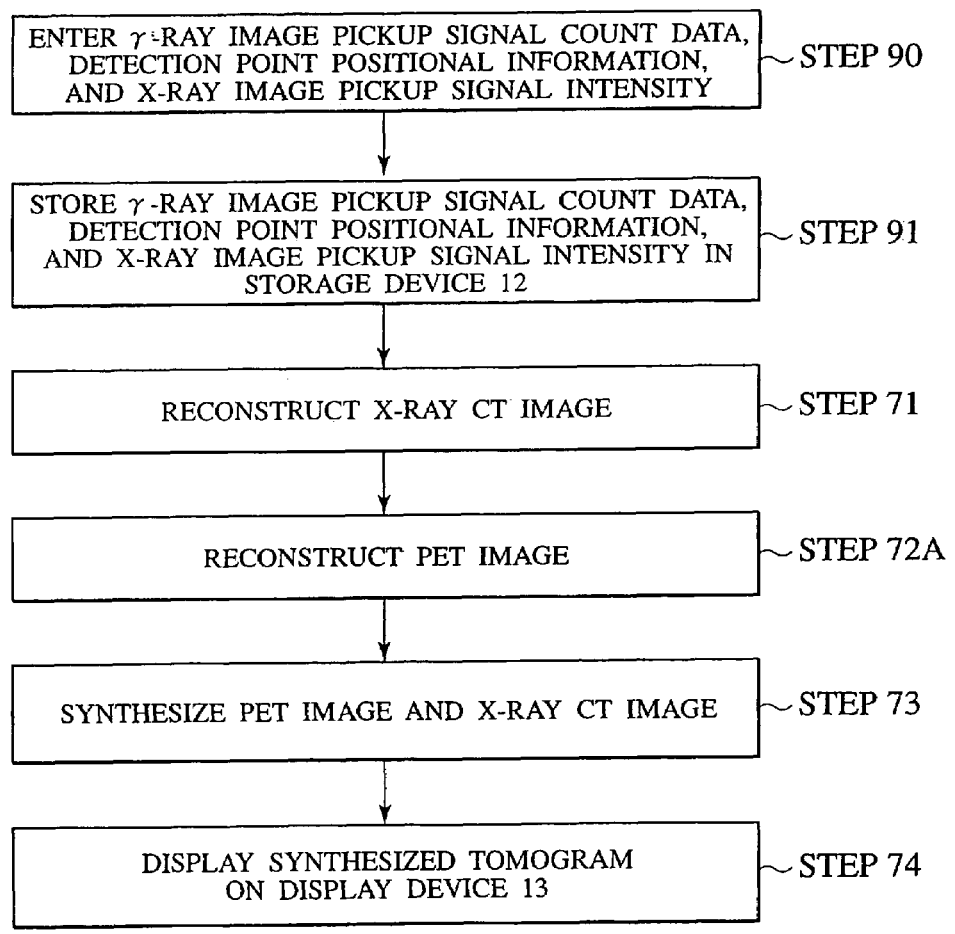

FIG.25

| | INPUT SIGNAL | OUTPUT SIGNAL |
|---|---|---|
| i | NO INPUT (0) | NO INPUT (0) |
| ii | TOTALLY ATTENUATED γ-RAYS (1) | NO OUTPUT (0) |
| iii | γ-RAYS WHOSE INCIDENCE POSITIONS AND DIRECTIONS ARE DETERMINED (1) | OUTPUT IN ACCORDANCE WITH INCIDENCE DIRECTIONS (1) |
| iv | TOTALLY ATTENUATED γ-RAYS (2) | OUTPUT IN ACCORDANCE WITH DIRECTION OF A STRAIGHT LINE THAT JOINS DETECTORS |
| v | γ-RAYS WHOSE INCIDENCE POSITIONS AND DIRECTIONS ARE DETERMINED (1) TOTALLY ATTENUATED γ-RAYS (1) | OUTPUT IN ACCORDANCE WITH INCIDENCE DIRECTIONS (1) |
| vi | γ-RAYS WHOSE INCIDENCE POSITIONS AND DIRECTIONS ARE DETERMINED (2) | IF INCIDENCES AGREE OR ROUGHLY AGREE IN DIRECTION, OUTPUT IS GENERATED IN ACCORDANCE WITH DIRECTION AGREED UPON (1) |
| | | IF INCIDENCES ARE ORIENTED IN DIFFERENT DIRECTIONS, OUTPUT IS GENERATED IN ACCORDANCE WITH SUCH DIRECTIONS (2) |
| vii | ARBITRARY γ-RAYS (3) | NOT OUTPUT (0) |

US 7,627,082 B2

RADIOLOGICAL IMAGING APPARATUS

CROSS REFERENCE TO RELATED APPLICATIONS

The present application is a continuation of U.S. application Ser. No. 10/270,151, filed on Oct 15, 2002 now U.S. Pat. No. 7,297,958, the disclosure of which is herewith incorporated by reference in its entirety.

BACKGROUND OF THE INVENTION

The present invention relates to a radiological imaging apparatus, and more particularly to a radiological imaging apparatus ideally applicable to X-ray computed tomography, positron emission computed tomography (hereinafter referred to as "PET"), single-photon emission computed tomography (hereinafter referred to as "SPECT"), digital X-ray examination flat panel detector, and similar equipment.

Radiological imaging is a non-invasive imaging technology to examine physical functions and conformation of a medical examinee as a subject. Typical radiological imaging devices are X-ray computed tomography, digital X-ray examination, PET, and SPECT devices.

PET is a method for administering a radiopharmaceutical (hereinafter referred to as a "PET pharmaceutical") containing positron-emitting nuclides ($^{15}$O, $^{13}$N, $^{11}$C, $^{18}$F, etc.), which are radionuclides, to a medical examinee, and examining locations in the examinee's body where the PET pharmaceutical is heavily consumed. More specifically, the PET method is used to detect γ-rays that are emitted from the medical examinee's body due to the administered PET pharmaceutical. A positron emitted from the radionuclides contained in the PET pharmaceutical couples with an electron of a neighboring cell (cancer cell) to disappear, emitting a pair of γ-rays (paired γ-rays) having an energy of 511 keV. These γ-rays are emitted in directions opposite to each other (180°±0.6°). Detecting this pair of γ-rays using radiation detectors makes it possible to locate the two radiation detectors between which positrons are emitted. Detecting many of these γ-ray pairs makes it possible to identify the locations where the PET pharmaceutical is heavily consumed. For example, when a PET pharmaceutical produced by combining positron-emitting nuclides with glucose is used, it is possible to locate carcinomatous lesions having hyperactive glucose metabolism. The data obtained is converted to individual voxel data by the filtered back projection method, which is described on pages 228 and 229 of IEEE Transaction on Nuclear Science, Vol. 21. The half-life period of positron-emitting nuclides ($^{15}$O, $^{13}$N, $^{11}$C, $^{18}$F, etc.) used for PET examination ranges from 2 to 110 minutes.

In PET examination, γ-rays generated upon positron annihilation attenuate within the human body so that transmission data is imaged to compensate for γ-ray attenuation within the human body. Transmission data imaging is a method of measuring the γ-ray attenuation within the medical examinee's body by, for instance, allowing γ-rays to enter the examinee's body using cesium as a radiation source and measuring the radiation intensity prevailing after penetration through the examinee's body. The PET image accuracy can be enhanced by estimating the γ-ray attenuation within the examinee's body from the measured γ-ray attenuation rate and correcting the data derived from PET examination.

A method for increasing the PET examination accuracy is described on page 15 of Medical Imaging Technology, Vol. 18-1. This method is used to insert a reflection plate into a crystal, acquire the information about depth with a DOI (Depth-Of-Interaction) detector, and reconstruct the image according to the acquired information to improve the image quality. For the use of this method, it is necessary to use a radiation detector that is capable of acquiring the information about radiation detector's position in the direction of the depth.

However, the use of a DOI detector involves image deterioration, which is caused by a decrease in the amount of signal transmission substance. When, for instance, a 5 mm square BGO scintillator is used, approximately 200 photons are generated to function as a signal transmission substance when there is a 511 keV incident γ-ray. However, when photons are partly reflected by a reflection plate as in the use of the DOI detector noted above, the amount of signal transmission substance decreases. When the quantity of signal transmission substance reaching a photomultiplier tube is N and the incident γ-ray energy is E, the energy spectrum spread σ can be expressed by equation (1).

$$\sigma = E/\sqrt{N} \qquad (1)$$

Therefore, when the value N becomes smaller, the value σ increases to spread the energy spectrum. When the energy spectrum is spread, the correlation between the incident γ-ray energy and the signal generated by a DOI detector is impaired. As a result, this makes it difficult to accurately measure the incident γ-ray energy.

If incident γ-ray energy measurements cannot be accurately made, it is difficult to remove scattered radiation contained in incident γ-rays. In PET, the signal output from a radiation detector is passed through an energy filter for scattered radiation removal so as to detect only γ-rays that have a specific energy level or higher. However, if the energy spectrum is spread and, for example, the radiation detector signal output generated by 511 keV γ-rays cannot be differentiated from the radiation detector signal output generated by 300 keV γ-rays, it is necessary to use an energy filter rated at 300 keV or lower. In this instance, 300 keV or higher scattered radiation is also measured so that the amount of noise increases. This can cause PET image deterioration.

SPECT is a method for administering a radiopharmaceutical (hereinafter referred to as a "SPECT pharmaceutical") containing single-photon-emitting nuclides ($^{99}$Tc, $^{67}$Ga, $^{201}$Tl, etc.), which are radionuclides, and glucose or other substance that gathers around specific tumors or molecules, to a medical examinee, and detecting a γ-ray emission from radionuclides with a radiation detector. The energy of γ-ray emission from single-photon-emitting nuclides, which are frequently used for SPECT examination, is approximately several hundred keV. In SPECT, a single γ-ray is emitted so that the angle of γ-ray incidence upon a radiation detector cannot be determined. Therefore, a collimator is used to obtain angular information by detecting only the γ-radiation incident at a specific angle. The SPECT is an examination method for detecting γ-rays generated within a medical examinee's body due to the SPECT pharmaceutical for the purpose of identifying the locations where the SPECT pharmaceutical is heavily consumed. The data obtained is converted to individual voxel data by the filtered back projection or like method as is the case with PET. It should be noted that transmission images may also be generated in SPECT. The half-life period of $^{99}$Tc, $^{67}$Ga, and $^{201}$Tl, which are used for SPECT, is longer than that of PET radionuclides and from 6 hours to 3 days.

X-ray CT (computed tomography) is a method for exposing a medical examinee to radiation emitted from a radiation source and imaging the conformation within the examinee's body in accordance with radiation transmittance in the examinee's body. The intensity of X-rays passing through the examinee's body, which is measured with a radiation detector, is used to determine the coefficient of linear attenuation within the examinee's body between the X-ray source and radiation detector. The determined linear attenuation coefficient is used to determine the linear attenuation coefficient of each voxel by the aforementioned filtered back projection method. The resulting value is then converted to a CT value.

A flat panel detector is a flat radiation detector for use in digital X-ray examination, which is a digital version of conventional X-ray examination. Being equipped with such a flat radiation detector instead of a conventional X-ray film, a flat panel detector imaging device detects X-rays passing through a medical examinee's body, handles the information about attenuation within the examinee's body as digital information, and displays the digital information on a monitor. The flat panel detector imaging device does not require the use of X-ray film or other media and displays an image immediately after image exposure.

For maintenance of examination accuracy, all these radiological imaging apparatuses require their radiation detectors to be subjected to detection efficiency calibration at periodic intervals of, for instance, three months. The radiation detector's detection efficiency deteriorates with time. However, the deterioration characteristic varies from one radiation detector to another. It is therefore necessary to determine the detection efficiency of each radiation detector on a periodic basis. In PET or SPECT examination in which the number of photons incident on each radiation detector is measured, correct measurement cannot be made if the detection efficiency varies from one radiation detector to another. Therefore, the detection efficiency of each radiation detector is determined beforehand, and the value of each radiation detector is multiplied by the reciprocal of the determined detection efficiency value in order to compensate for image deterioration resulting from the detection efficiency variation of radiation detectors. In X-ray CT or flat panel detector examination, on the other hand, the X-ray intensity is detected by radiation detectors; however, intensity measurements need to be corrected if the detection efficiency varies.

As explained above, the use of radiological imaging apparatuses entails an enormous amount of time and labor because they require their radiation detectors to be checked for detection efficiency variation in order to maintain examination accuracy.

SUMMARY OF THE INVENTION

It is an object of the present invention to provide a radiological imaging apparatus that determines the locations reached by radiation with increased precision and enhances the accuracy of images to be generated.

The present invention to attain the above-described object is characterized by comprising an image pickup device, which comprises a plurality of radiation detectors for detecting radiation from a subject, wherein the radiation passing through a first radiation detector is to be detected by a second radiation detector. Since the second radiation detector is provided to detect the radiation passing through the first radiation detector, the locations reached by radiation (locations at which radiation is detected) can be confirmed, with increased precision, in the direction of the depth from the first radiation detector opposing the subject. As a result, a highly accurate image depicting the interior of the subject's body can be obtained.

Preferably, the present invention comprises a plurality of radiation detectors that enable an image pickup device to detect radiation from a subject, wherein the radiation detectors are formed in the image pickup device and positioned around the circumference of the through-hole, into which a bed is to be inserted, and at different radial locations.

Preferably, the present invention also comprises a plurality of radiation detectors that enable an image pickup device to detect radiation from a subject, wherein the radiation detectors are mounted on radiation detector support members that are positioned around the circumference of the through-hole, into which a bed is to be inserted, and at different radial locations.

In addition, the present invention attaining the above-described object is characterized by comprising a plurality of radiation detectors for γ-ray detection, wherein a radiation detector detecting unscattered internal γ-rays is located within a preselected period of time and in accordance with the detection signals output from at least three radiation detectors and the position information about these radiation detectors.

The present invention makes it possible to find the sequence of unscattered γ-ray attenuation (scatter sequence) in accordance with three or more detection signals output within a preselected period of time and the positional information about three or more radiation detectors that generated the detection signals, and determine the position and direction of γ-ray initial incidence. In marked contrast to determining the γ-ray initial incidence position in a random manner, the present invention is capable of locating unscattered γ radiation with high efficiency and generating highly accurate tomograms.

In addition, the present invention attaining the above-described object is characterized in that it comprises a plurality of radiation detectors for γ-ray detection, and that when detection signals are output from at least three of such radiation detectors within a preselected period of time, the attenuation sequence, initial incidence position, and initial incidence direction of one of paired γ-rays are determined in accordance with the positional information about at least two of such radiation detectors, the energy detection values of at least two of such radiation detectors, and the positional information about a radiation detector detecting the remaining γ radiation of paired γ-rays.

The present invention determines the attenuation sequence (scatter sequence) of one of paired γ-rays in accordance with the positional information about the remaining paired γ-ray, and determines the position and direction of γ-ray initial incidence on a radiation detector. More specifically, the positional information about each radiation detector detecting a first one of paired γ-rays and the positional information about a radiation detector detecting the remaining paired γ-ray are used to estimate two or more possible attenuation sequences of the first one of the paired γ-rays. The estimated attenuation sequences are examined to choose the one that exhibits the proper correlation between the scatter angle and energy detection value of the first one of the paired γ-rays. The γ-ray attenuation sequence is determined in this manner. As a result, the position of initial γ-ray incidence on a radiation detector (the position of a radiation detector related to the first γ-ray attenuation) is determined. Consequently, it is possible to conclude that a γ-ray generation source (diseased area) exists on a straight line (direction of initial incidence) joining the located radiation detector and the radiation detector detecting the remaining paired γ-ray. In marked contrast to determining the γ-ray initial incidence position in a random manner, the present invention is therefore capable of locating unscattered γ radiation with high efficiency and generating highly accurate PET images.

In addition, the present invention attaining the above-described object is characterized in that it comprises a plurality of radiation detectors for γ-ray detection and collimators mounted in front of the radiation detectors to permit γ-ray passage, and that when detection signals are output from at least three of such radiation detectors within a preselected period of time, the attenuation sequence, initial incidence position, and initial incidence direction of γ radiation are determined in accordance with the positional information about at least three of such radiation detectors and the energy detection values of at least three of such radiation detectors.

When the detection signals of three or more radiation detectors are simultaneously counted (output within the specified period of time), the present invention determines the γ-ray attenuation sequence (scatter sequence in accordance with the positional information about the three or more detection signals and the energy detection values from the three or more radiation detectors, and determines the position and direction of γ-ray incidence on a radiation detector. More specifically, the above-mentioned positional information is first used to estimate two or more possible sequences of γ-ray attenuation, and the estimated sequences are checked to choose the one that exhibits the proper correlation with the above-mentioned energy detection values. In accordance with the determined γ-ray initial incidence position and the above energy detection values, the direction of γ-ray initial incidence can be determined. In marked contrast to determining the γ-ray initial incidence position in a random manner, the present invention is therefore capable of locating unscattered γ radiation with high efficiency and generating highly accurate PET images.

BRIEF DESCRIPTION OF THE DRAWINGS

FIG. 13 is a flow chart illustrating a tomogram generation process that is performed by a computer shown in FIG. 10;

FIG. 20 is a flow chart illustrating a tomogram generation process that is performed by a computer shown in FIG. 17;

FIG. 25 shows a typical signal input/output of a coincidence counter according to the embodiment shown in FIG. 23.

DETAILED DESCRIPTION OF THE PREFERRED EMBODIMENTS

Embodiment 1

Figure 1:
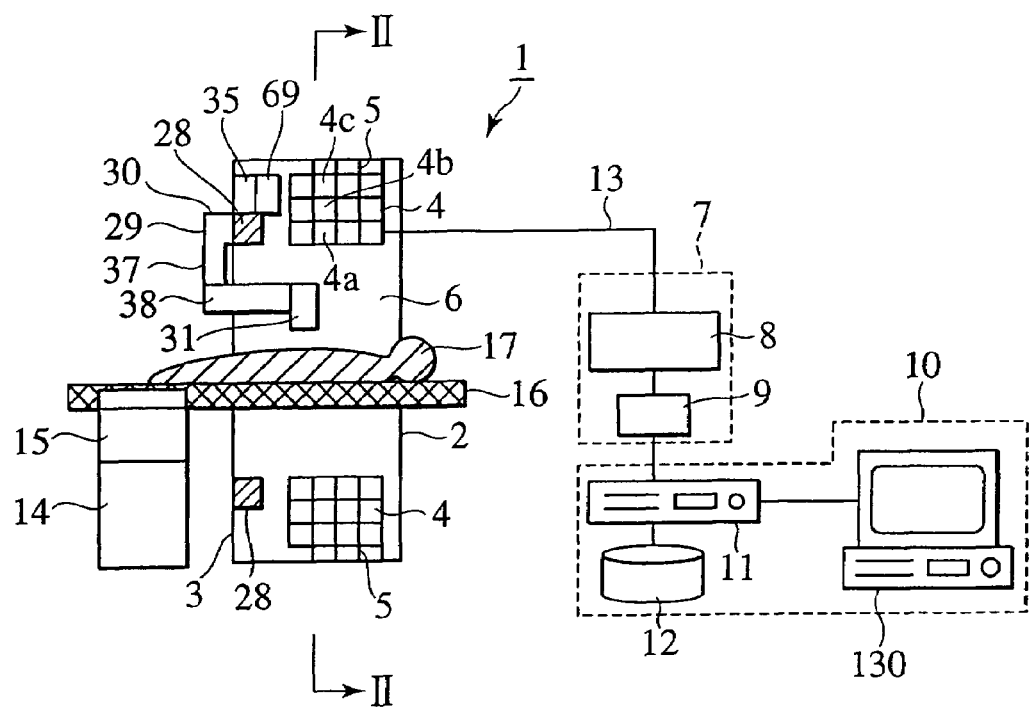
FIG. 1 is a configuration diagram showing a radiological imaging apparatus according to a preferred embodiment of the present invention.
Figure 2:
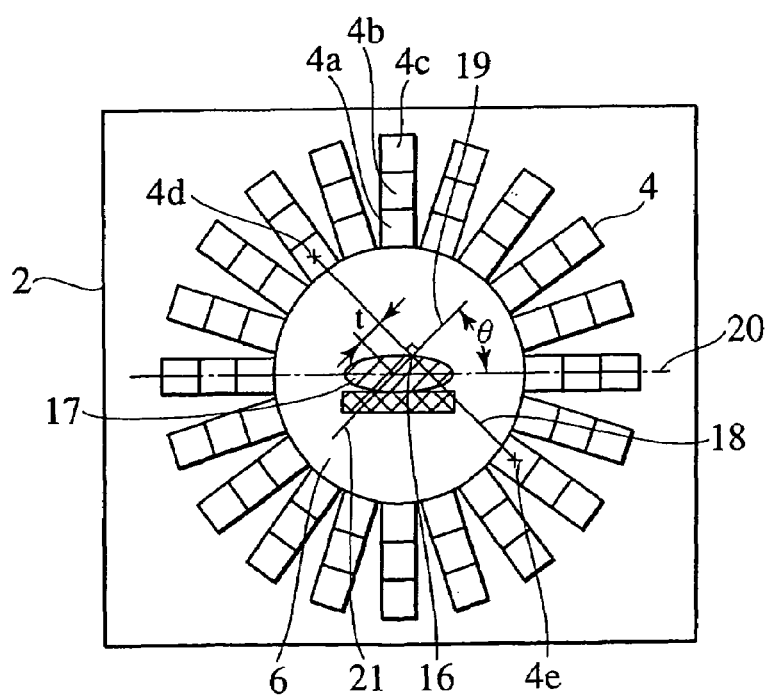
FIG. 2 is a cross sectional view taken along line II-II of FIG. 1.

A radiological imaging apparatus according to a preferred embodiment of the present invention will be described below with reference to FIGS. 1 and 2. A radiological imaging apparatus 1 of Embodiment 1 is used for PET examination. This apparatus comprises an image pickup device 2, a signal processor 7, a tomogram generator 10, a medical examinee-holding device 14, a calibrated radiation source circumferential transfer unit 37, and a drive controller 35.

The image pick device 2 has a casing 3, a large number of radiation detectors 4, and a large number of radiation detector support plates 5. The casing 3 has an opening (through-hole) 6 into which a medical examinee or a subject is to be inserted. A large number of the radiation detectors (e.g., 10,000 radiation detectors in total) 4 are positioned around the circumference of the through-hole 6 and arranged in the axial direction of the through-hole 6. As shown in FIG. 2, the innermost radiation detectors 4 are circularly disposed around the circumference of the through-hole 6. The other radiation detectors 4 are arranged radically from the center of the through-hole 6 with the above-mentioned innermost radiation detectors 4 regarded as the starting points. The radiation detectors 4 are also disposed at their respective different positions in the radial directions of the through-hole 6. That is, Embodiment 1 is configured so that multiple sets of three radiation detectors 3 (e.g., the radiation detectors 4a, 4b, and 4c shown in FIG. 2) are linearly positioned to form three layers in the radial direction of the through-hole 6. Each layer of radiation detectors 4 is positioned in a circular form (e.g., concentrically).

Figure 3:
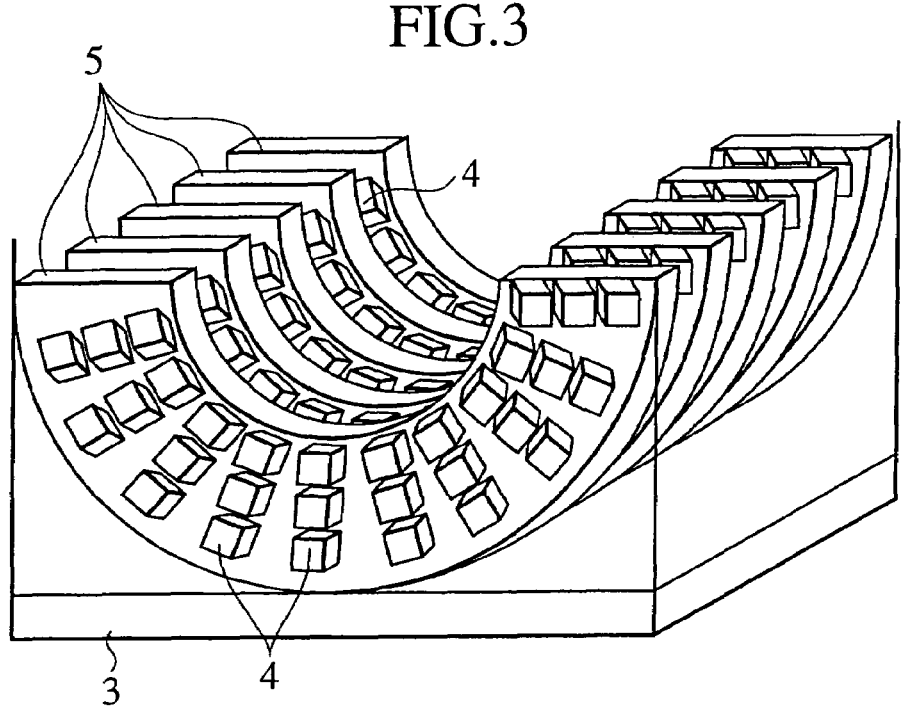
FIG. 3 is a perspective view illustrating the structure of a radiation detector support shown in FIG. 1.

As shown in FIG. 3, the radiation detectors 4 are mounted on a lateral surface of the radiation detector support plate 5. More specifically, the radiation detectors 4 are radically mounted on a lateral surface of the radiation detector support plate 5, which is shaped like a half ring. A plurality of radiation detector support plates 5, on which the radiation detectors are mounted, are mounted on the lower inner surface of the through-hole 6 and arranged in the axial direction of the through-hole 6. These radiation detector support plates 5 are fastened to the casing 3. Although not shown in FIG. 3, a plurality of radiation detector support plates 5, on which the radiation detectors 4 are mounted, are also mounted on the upper inner surface of the through-hole 6, arranged in the axial direction of the through-hole 6, and fastened to the casing 3. One radiation detector support plate 5 mounted on the lower inner surface of the through-hole 6 and one radiation detector support plate 5 mounted on the upper inner surface of the through-hole 6 are positioned so as to form a ring in the same plane. The radiation detector support plates 5 may also be shaped in a circular form.

The signal processor 7 comprises γ-ray discriminators 8 and a coincidence counter 9 provided for each of the radiation detectors 4. The γ-ray discriminators 8 are connected to their respective radiation detectors 4 via a wiring 13. The number of installed γ-ray discriminators 8 is equal to that of installed radiation detectors 4. The coincidence counter 9 is connected to all the γ-ray discriminators 8. The tomogram generator 10 comprises a computer 11, a storage device 12, and a display device 130. The computer 11 is connected to the coincidence counter 9. The storage device 12 is connected to the computer 11. The display device is also connected to the computer 11. The medical examinee-holding device 14 is provided with a support 15 and a bed 16, which is mounted on the top of the support 15 so as to be moved in the longitudinal direction. The image pickup device 2 is disposed in a direction perpendicular to the longitudinal direction of the bed 16.

Typical examples of a radiation detector include a semiconductor radiation detector and a scintillator. The scintillator is not suitable for a multilayer arrangement (e.g., aforementioned three layers) because a photomultiplier or like device needs to be mounted on the rear of a crystal (BGO, NaI, etc.), which serves as a radiation detector. On the other hand, the semiconductor radiation detector is suitable for a multilayer arrangement because it does not require the use of a photomultiplier or like device. In Embodiment 1, semiconductor radiation detectors are used as the radiation detectors 4, and their detection unit, which is a 5 mm cube, is made of cadmium telluride (CdTe). The detection unit may also be made of gallium arsenide (GaAs) or cadmium zinc telluride (CZT).

Figure 4B:
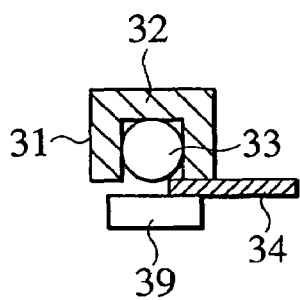
FIG. 4B is a cross sectional view taken along line IV-IV of FIG. 4A.
Figure 4A:
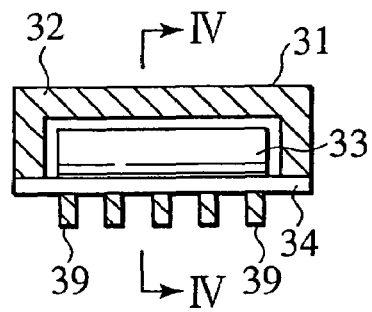
FIG. 4A is a longitudinal sectional view of a calibrated radiation source shown in FIG. 1.

The calibrated radiation source circumferential transfer unit 37 includes a guide rail 28 and a calibrated radiation source device 29. The guide rail 28 is circular, mounted on a lateral surface of the medical examinee holding device 14 on the casing, and arranged around the circumference of the through-hole 6. The calibrated radiation source device 29 has a calibrated radiation source drive 30 and a calibrated radiation source 31. The calibrated radiation source drive 30 is movably mounted on the guide rail 28. Although not shown in the figure, the calibrated radiation source drive 30 includes a pinion that engages with a rack on the guide rail 28, and a motor that rotates the pinion via a speed reduction mechanism. The calibrated radiation source 31 is mounted on the casing a (not shown) for the calibrated radiation source drive 30 and attached to the distal end of an arm 38 that is horizontally telescopic. As shown in FIGS. 4A and 4B, the calibrated radiation source 31 houses a γ-ray source 33 within a γ-ray shield 32 having a unidirectional opening. Except the above-mentioned opening, the external surface of the γ-ray shield 32 is covered by a casing (not shown) serving as an enclosure. The calibrated radiation source 31 includes a movable shutter 34, which is capable of covering the opening in the γ-ray shield 32. A Ga—Ge radiation source for 511 keV γ-ray emissions is used as the γ-ray source 33. A Cs radiation source for 662 keV γ-ray emissions may be used instead of the Ga—Ge radiation source. The calibrated radiation source 31 is a radiation source for use during transmission data imaging. A collimator 39 that is positioned in front of the opening in the γ-ray shield 32 is mounted on the γ-ray shield 32 so as not to obstruct the open/close operation of the shutter 34.

First of all, transmission data imaging by a radiological image apparatus 1A will be described. Transmission data imaging is a technique for measuring the γ-ray transmittance with a medical examinee's body with a calibrated radiation source. The time required for measurement is about 1 or 2 minutes. After γ-rays emitted from the calibrated radiation source pass through a medical examinee, they are measured by radiation detectors 4. The rate of γ-ray attenuation within the medical examinee's body is determined in accordance with the radiation intensity of the calibrated radiation source and the measured γ radiation. The determined γ-ray attenuation rate is used to compensate for an in-vivo scatter (phenomenon in which γ-rays generated within a medical examinee's body due to a radiopharmaceutical are scattered and attenuated) during PET examination.

The details of transmission data imaging will be described below. The medical examinee 17 laid on the bed 16 is inserted into the through-hole 6. When transmission data imaging starts, the radiation source controller 69 opens the shutter 34. γ-rays emitted from the γ-ray source 33 pass through the opening in the γ-ray shield 32 and collimator 39, and then fall on the medical examinee 17. The directivity of γ-rays emitted from the γ-ray source 33 is increased by the collimator 39 so that the direction of γ-ray travel is determined. At the beginning of transmission data imaging, the drive controller 35 outputs a drive start signal to rotate the motor of the calibrated radiation source drive 30. When the motor rotates, the calibrated radiation source drive 30 moves on a guide rail 28 to circulate around the medical examinee 17. Within the through-hole 6, the calibrated radiation source 31 moves around the medical examinee 17. Therefore, highly directional γ-rays emitted from the calibrated radiation source 31 are incident on the medical examinee 17 from all circumferential positions. The bed 16 moves toward the opposite end of the through-hole 6. After γ-rays pass through the medical examinee 17, they are measured by the radiation detectors 4. Since highly directional γ-rays are emitted, unscattered γ-rays are measured by the radiation detectors 4. These rays have the same 511 keV energy as when they are emitted from the γ-ray source 33.

The radiation detectors 4 measure the γ-rays passing through the medical examinee 17 and output a γ-ray detection signal. In response to this γ-ray detection signal, the γ-ray signal discriminator 8 generates a pulse signal as is the case with the γ-ray detection signal detected during PET examination described later. The coincidence counter 9 measures the pulse signal and outputs its count and the two points of paired γ-ray detection (the positions of a pair of radiation detectors 4 that are mounted about 180° apart from each other with respect to the axial center of the through-hole 6). The computer 11 stores the count and the positional information about the two detection points in the storage device 12. At the end of transmission data imaging, the drive controller 35 outputs a drive end signal to stop the motor of the calibrated radiation source drive 30. At this time, the radiation source controller 69 closes the shutter 34 of the calibrated radiation source 31 so as to prevent γ-rays from being emitted outside.

Three radiation detectors that are linearly arranged in the direction of the radius of the through-hole 6 to form three layers (e.g., radiation detectors 4a, 4b, and 4c shown in FIG. 1) are handled as a radiation detector group. Embodiment 1 provides a plurality of radiation detector groups. When the energy of emitted γ-rays is uniform, the γ-ray detection efficiency is determined by a theoretical formula. Since the radiation detectors 4 are semiconductor radiation detectors having a detection unit made of 5 mm thick CdTe, the detection efficiency of 511 keV γ-rays is about 20%. In a single radiation detector group, therefore, incident γ-radiation is attenuated by about 20% in the first layer radiation detector 4, and the 80% γ-radiation passing through the first layer radiation detector 4 is attenuated by about 20% in the second layer radiation detector 4, that is, about 16% γ-radiation attenuation occurs in the second layer radiation detector 4. In the third layer radiation detector 4, the 64% γ-radiation passing through the second layer radiation detector 4 is attenuated by about 20%, that is, about 12.8% γ-radiation attenuation occurs. γ-ray detection signals reflecting such attenuations are output from the first and second layer radiation detectors 4. These γ-ray detection signals are fed to the γ-ray discriminators 8 of the associated signal processors 7, subjected to a scattered γ-ray removal process, and converted to pulse signals. The coincidence counters 9 of the signal processors 7 measure the pulse signals. When the γ-ray detection signals fed from the layered radiation detectors 4 are independently measured and the measurement result significantly differs (by, for instance, more than ±5%) from the theoretical detection efficiency proportion (approx. 20:16:12.8) of the first-layer to third-layer radiation detectors 4, it means that the detection efficiency of one or more of the radiation detectors 4 is decreased due to radiation detector deterioration. If, for instance, one radiation detector 4 is deteriorated and the other two radiation detectors 4 are operating normally, the measured detection efficiency proportion of the affected radiation detector group greatly differs from the above-mentioned theoretical value. It is therefore possible to locate the radiation detector 4 that is deteriorated. Further, the percentage of detection efficiency decrease caused by deterioration can be calculated from the detection efficiencies, detection efficiencies determined from the above-mentioned proportion, and measured detection efficiencies of the two normal radiation detectors 4. When, for instance, the measured detection efficiency proportion determined from the measurements of three radiation detectors in one radiation detector group is 20:4:12.8, the measured detection efficiency of the second layer radiation detector 4 is 12 points lower (75% lower) than the theoretical detection efficiency. It means that the second layer radiation detector is faulty.

The concept of fault detection will be described below. When γ-rays are emitted from the γ-ray source 33 at a certain time, they are incident on three radiation detectors 4 in one radiation detector group (e.g., radiation detectors 4a, 4b, and 4c shown in FIG. 2) but not on the three radiation detectors 4 in another radiation detector group (e.g., a radiation detector group adjacent to the first one). The detection efficiency proportion of the radiation detectors 4 in a single radiation detector group is determined from the data indicating the previous deterioration of the radiation detectors 4 while considering the γ-ray transmission distance and γ-ray transmission sequence. Further, the theoretical detection efficiency proportion of the radiation detectors 4 in the radiation detector group is determined by performing a simulation or theoretical calculations. The measured detection efficiency proportion determined according to the γ-ray detection signals generated from the radiation detectors 4 in the radiation detector group is compared with the above-mentioned theoretical detection efficiency proportion to check whether or not the radiation detectors 4 in the radiation detector group are deteriorated. All the radiation detector groups are subjected to the comparison between the measured detection efficiency proportion and the above-mentioned theoretical detection efficiency proportion. If all the radiation detectors 4 mounted on the image pickup device 2 are of the same type, the theoretical detection efficiency proportion can be determined by performing calculations on only one representative radiation detector group. Further, the measured detection efficiency proportion determined from the individual γ-ray detection signals is compared with the detection efficiency proportion determined from the data indicating the previous deterioration of the radiation detectors 4 to check the progress of deterioration of the radiation detectors 4 in the radiation detector group. If the radiation detectors 4 are deteriorated, the storage device 12 stores the information about the degree of deterioration, and the user is notified of deterioration and fault. When this process is repeated for all radiation detector groups, it is possible to grasp the degree of detection efficiency deterioration of the individual radiation detectors mounted on the image pickup device 2 and remove faulty radiation detectors. A specific process based on the above-described concept of fault detection will be described later with reference to FIGS. 5 and 6.

Next, a PET examination process performed with the radiological imaging apparatus 1 will be described. A PET pharmaceutical is injected into or otherwise administered to the medical examinee 17 or the subject in advance. The medical examinee 17 stands by for a predetermined period of time so that the PET pharmaceutical is diffused within its body and gathered at a diseased area (e.g., carcinomatous lesion) to permit imaging. An appropriate PET pharmaceutical is selected in accordance with a lesion to be checked for. When the predetermined period of time elapses, the medical examinee 17 is laid on the bed 16 and subjected to PET examination with the image pickup device 2. When PET examination starts, the bed 16 moves toward the image pickup device 2 and goes into the through-hole 6, carrying the medical examinee 17 into the through-hole 6. When 511 keV γ-rays (in the case where the PET pharmaceutical contains $^{18}$F) are emitted from a lesion in the body of the medical examinee 17, they are incident on the radiation detectors 4. The radiation detectors 4 detect γ-rays that are emitted from the lesion due to PET pharmaceutical administration, and generate γ-ray detection signals. The γ-ray detection signals are delivered to the associated γ-ray discriminators 8 via the associated wiring 13. Each γ-ray discriminator includes a waveform shaper (not shown). The waveform shaper converts an input γ-ray detection signal to a γ-ray detection having a time Gaussian distribution waveform. The energy of γ-rays generated upon annihilation (at the lesion) of positrons emitted from the PET pharmaceutical is 511 keV. However, if the γ-rays are scattered within the body of the medical examinee, the energy is lower than 511 keV. To remove scattered γ-rays, the γ-ray discriminator 8 includes a filter (not shown) for selecting an energy setting of, for instance, 400 keV, which is lower than 511 keV, and passing γ-ray detection signals having a energy value greater than the energy setting. This filter receives the γ-ray detection signals that are output from the waveform shaper. An energy setting of 400 keV is selected here as an example in consideration of the variation of γ-ray detection signals generated upon 511 keV γ-ray incidence on the radiation detectors 4. In response to a γ-ray detection signal passing through the filter, the γ-ray discriminator 8 generates a pulse signal having a predetermined energy level.

The coincidence counter 9 receives pulse signals generated by all the γ-ray discriminators 8, and determines the count data for the γ-ray detection signals output from the radiation detectors 4. Further, the coincidence counter 9 uses the pulse signals for the aforementioned paired γ-rays to determine the positional information about two points of paired γ-ray detection. The positional information about these detection points is transmitted to the computer 11 and stored into the storage device 12 by the computer 11. The count data for the abovementioned γ-ray detection signals are also stored into the storage device 12 by the computer 11.

Figure 5:
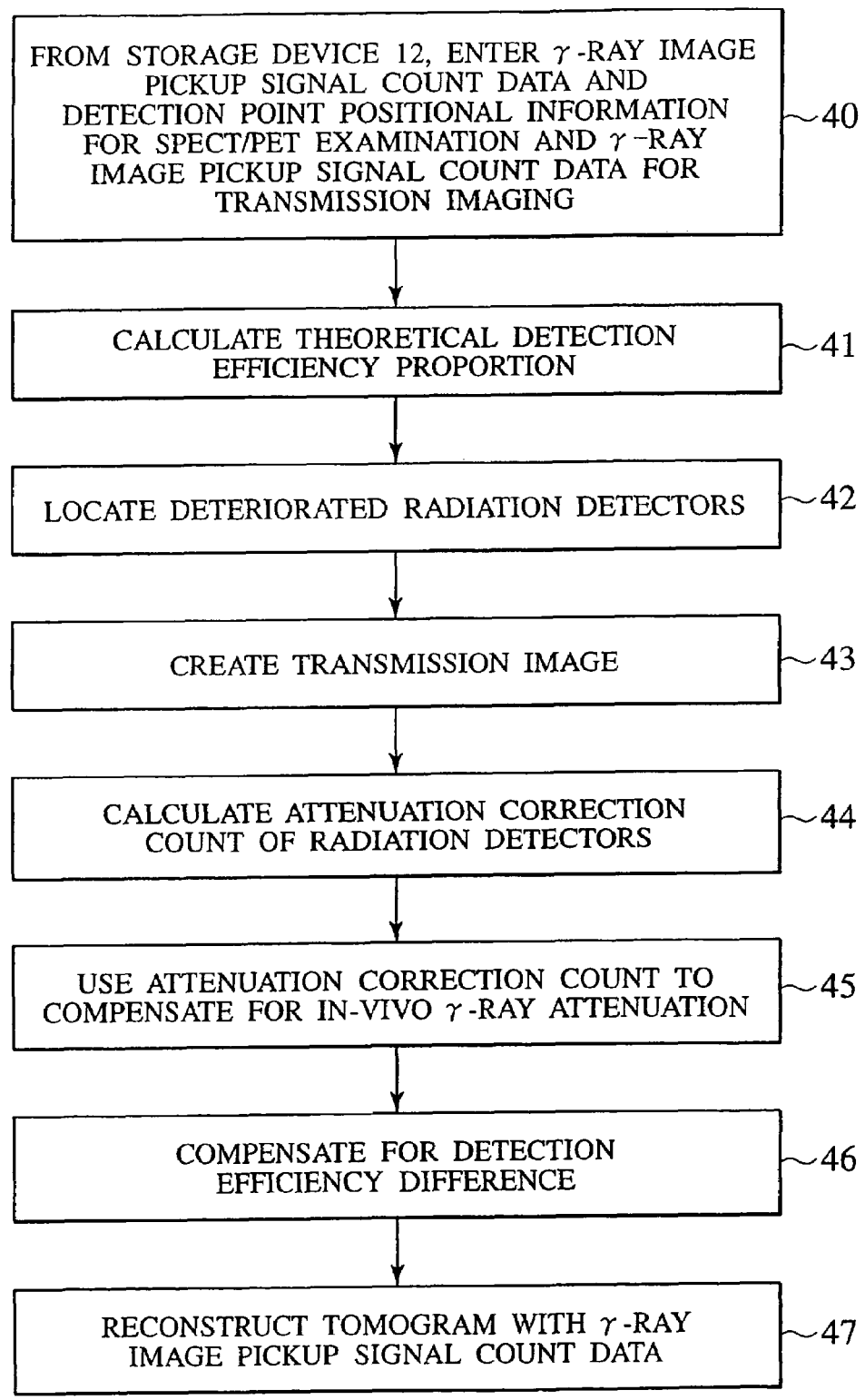
FIG. 5 is a flow chart illustrating a tomogram generation process that is performed by a computer shown in FIG. 1.
Figure 6:
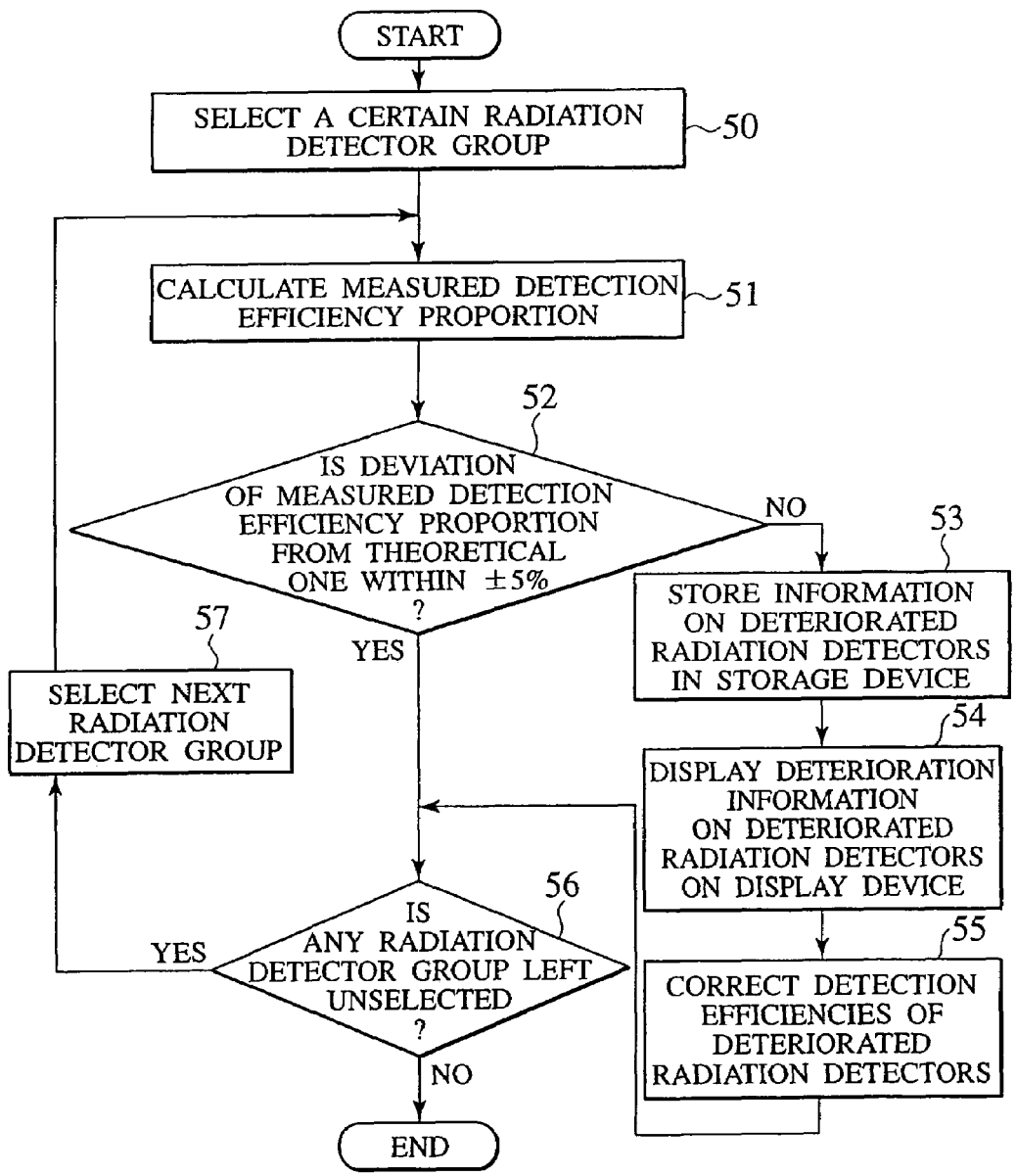
FIG. 6 is a flow chart that details the process performed in step 42 shown in FIG. 5.

The computer 11, using the count data and other relevant data, performs a processing procedure indicated in FIGS. 5 and 6 to reconstruct a tomogram of the medical examinee 17. The processing procedure will be detailed below. The count data derived from PET examination, the positional information about the associated detection points, and the count data derived from transmission imaging are read from the storage device 12 and input (step 40). The theoretical detection efficiency proportion of the radiation detectors in a radiation detector group is calculated (step 41). This theoretical proportion is determined by performing theoretical calculations on the transmission distance of γ-rays emitted from the medical examinee 17 (this distance varies with the radionuclides contained in the PET pharmaceutical) and the sequence of γ-ray transmission. When a PET pharmaceutical containing $^{18}$F is administered to the medical examinee 17, the theoretical detection efficiency proportion of three radiation detectors 4 in the radiation detector group is about 20:16:12.8. Unlike Embodiment 1 in which the theoretical detection efficiency proportion is calculated each time, the theoretical detection efficiency proportion of all the radiation detectors in the radiation detector group may be calculated in advance for various PET pharmaceuticals containing different radionuclides and stored in the storage device 12.

Next, deteriorated radiation detectors 4 are checked for (step 42). The process in step 42 is performed on a radiation detector group basis and will be described in detail with reference to FIG. 6. First, a radiation detector group is selected (step 50). The measured detection efficiency proportion of radiation detectors in the selected radiation detector group is calculated (step 51). More specifically, the count data derived from γ-ray detection signals output from the radiation detectors 4 in the selected radiation detector group are used to calculate the measured detection efficiency proportion of the radiation detectors. The difference between the measured detection efficiency proportion and theoretical detection efficiency proportion is checked to determine whether it is within a preselected range (+5% of the theoretical proportion) (step 52). When the difference is within the preselected range (when the answer to the question is "Yes"), the radiation detectors 4 in the selected radiation detector group are operating normally without being deteriorated. However, if the difference is outside the preselected range (when the answer to the question is "No"), the information about deteriorated radiation detectors 4 in the radiation detector group (these detectors are referred to as deteriorated radiation detectors) is stored in the storage device 12 (step 53). When the difference is outside the preselected range in this manner, it means that one or more radiation detectors 4 in the radiation detector group are deteriorated. Deteriorated radiation detectors in the radiation detector group can be located by comparing the measured detection efficiency proportion values of the radiation detectors with their theoretical ones as explained earlier. Next, the deterioration information about a deteriorated radiation detector 4 is output to the display device 130 (step 54). The deterioration information about the deteriorated radiation detector 4 is the detection efficiency proportion information that is obtained using the data indicating the degree of previous deterioration of the radiation detector 4. In accordance with the deterioration information about the deteriorated radiation detector 4, which is shown on the display device 130, the operator is able to grasp the degree of deterioration of the deteriorated radiation detector 4 on the basis of the deterioration information about the deteriorated detector 4 displayed on the display device 130. If a deteriorated radiation detector 4 is significantly deteriorated, it needs to be replaced by a new radiation detector. The detection efficiency of the deteriorated radiation detector 4 is corrected (step 55). If, for instance, the measured proportion values of radiation detectors 4a and 4c in a radiation detector group coincide with the theoretical ones and the measured proportion value of radiation detector 4b is considerably smaller than the theoretical one, the detection efficiency of radiation detector 4b is corrected to a detection efficiency that can be estimated from the measured detection efficiency proportion of radiation detectors 4a and 4c and the theoretical detection efficiency proportion of radiation detectors 4a, 4b, and 4c. The count data determined according to the corrected detection efficiency is stored in the storage device 12 as the count data about the radiation detector 4b.

When the answer to the question in step 52 is "Yes" or when the process in step 55 is terminated, it is checked whether or not "any radiation detector groups remain to be selected" (step 56). When the answer to the question in step 56 is "Yes", the next radiation detector group is selected in step 57. The processing from steps 51 onward is performed until the answer to the question in step 56 changes to "No". When the answer to the question in step 56 is "No", a transmission image is created (step 43). More specifically, the count data for γ-ray detection signals obtained at the time of transmission data imaging is used to calculate the γ-ray attenuation rate of each voxel in the body of the medical examinee 17. The γ-ray attenuation rate of each voxel is stored in the storage device 12.

Figure 7:
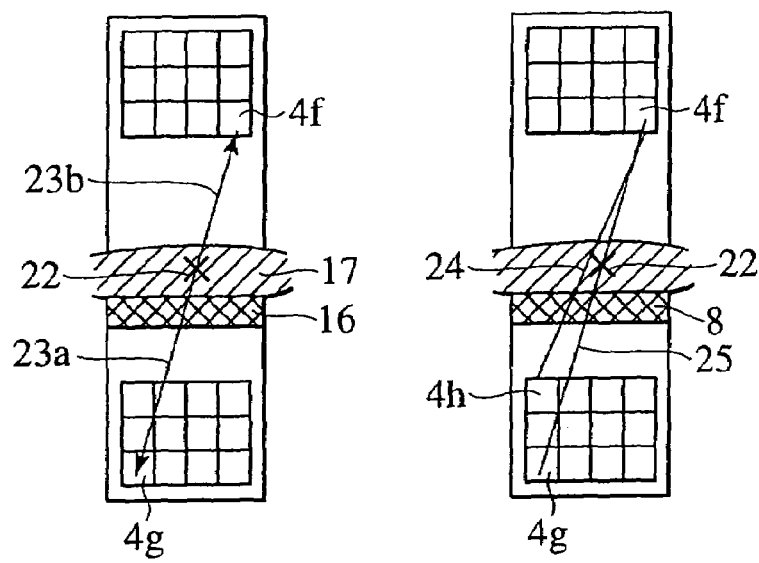
FIG. 7 presents diagrams that indicate how γ-rays are detected in an embodiment shown in FIG. 1.

Next, the in-vivo attenuation correction count for radiation detectors is calculated (step 44). Since paired γ-rays is emitted during the PET examination, the in-vivo attenuation correction count is calculated according to the sum of paired γ-ray move distances within the body. The count data derived from the PET examination, the positional information about detection points, the γ-ray attenuation rate calculated in step 43 are used to reconstruct the tomogram of the medical examinee 17 by the tomogram reconstruction method described later in step 47. First of all, the γ-ray attenuation rate of each voxel, which is obtained in step 43, is used to determine the rate of γ-ray attenuation between a pair of radiation detectors 4 (e.g., radiation detectors 4f and 4g shown in FIG. 7B), which detects paired γ-rays, according to the forward projection method. The reciprocal of the determined γ-ray attenuation rate is the attenuation correction count. In step 45, the attenuation correction count is used to provide an in-vivo attenuation correction. The count data derived from the PET examination is corrected by multiplying it by the attenuation correction count. Although the γ-rays generated at a lesion in the medical examinee 17 are absorbed and attenuated during its transmission through the body, the accuracy of the count data derived from the PET examination can be increased by correcting the count data with the above attenuation correction count.

In step 46, a γ-ray detection correction is also made in accordance with the detection efficiency difference among radiation detectors. Since paired γ-rays are emitted during the PET examination, the count data needs to be corrected using the detection efficiencies of two radiation detector groups at which respective paired γ-rays arrive. More specifically, the correction is made by multiplying the detection efficiency correction counts of radiation detectors that have detected γ-rays in the two radiation detector groups. This correction process will be detailed below. The difference between the theoretical and measured detection efficiencies of each radiation detector 4, which prevails during forward projection imaging, is determined in step 42. Let the theoretical detection efficiency value of the i-th radiation detector 4 in radiation detector group j, which prevails during forward projection imaging, be $Xfi_{ij}$, and the count data corrected in step 45 be $Xse_{ij}$. If the i-th detector is found to be faulty while the k-th detector is normal, the corrected PET count data $Xsi_{ij}$ for the i-th radiation detector is as expressed by equation (2). In order from the radiation detector 4 nearest the through-hole 6 to the radiation detector 4 farthest from the through-hole 6, the value i is 1, 2, 3, and so son.

$$Xsi_{ij}=Xse_{kj}\times Xfi_{ij}/Xfi_{kj} \quad (2)$$

The corrected PET count data (count data corrected in accordance with the detection efficiency difference among radiation detectors), which is calculated from equation (2), is stored in the storage device 12.

The tomogram of the medical examinee, which contains a diseased area (e.g., carcinomatous lesion), is reconstructed (step 47). In step 47, the tomogram is reconstructed using the corrected PET count data $Xsi_{ij}$, which is derived from the correction made in step 46, and the positional information about detection points. Tomogram reconstruction will be detailed below. The computer 11 performs a tomogram reconstruction process with the above count data and detection point positional information while using the filtered back projection method. The computer 11 is a device for tomogram reconstruction. When the filtered back projection method is used, the tomogram is reconstructed using data that is sorted according to two parameters (distance t and angle θ), as described in the aforementioned document. The distance t and angle θ will be detailed with reference to FIG. 2. Suppose that the paired γ-rays emitted from a lesion in the medical examinee 17 is detected by radiation detectors 4d and 4e. A straight line 19 passes through the middle point of a line 18, which joins radiation detectors 4d and 4e, and is at right angles to the line 18. The angle formed between a reference axis 20 (straight line oriented in any direction and passing through the central point of a circle on which innermost radiation detectors are positioned, that is, the central point of the through-hole 6) and the line 19 is θ. The distance between the central point 21 of the through-hole 6 and line 18 is t. The angle θ represents the angle of rotation of the line 18 that joins radiation detectors 4d and 4e, which have detected paired γ-rays, from the reference axis 20.

In the radiological imaging apparatus 1, a plurality of radiation detectors 4 is layered in the radial direction of the through-hole 6. Thanks to this layered arrangement, a new function described below can be exercised. For example, suppose that two γ-rays 23a, 23b, which are generated at an γ-ray generation point 22 (lesion) in the body of the medical examinee 17 as shown in FIG. 7A, are incident on radiation detectors 4f and 4g. Since the attenuation positions within the detectors are unknown, a line joining the ends of a pair of radiation detectors 4f, 4h, that is, a line 24 shown in FIG. 7B is regarded as a detection line when a conventional method is used. The radiological imaging apparatus 1, on the other hand, layers radiation detectors 4 in the radial direction of the through-hole 6. Therefore, the γ-ray detection signal of radiation detector 4g, which is located outward in the radial direction, is obtained so that a line 25, which joins radiation detectors 4f and 4g, can be used as a detection line. In other words, the attenuation position in the direction of a detector depth can be determined although it could not be determined through the use of a conventional detector. As a result, the image accuracy is increased because the detection line 25 accurately passes a location of paired γ-ray generation. Further, measured data accuracy increases because the detection line is positioned closer to an actual location of paired γ-ray generation.

Next, the obtained result is reconstructed by the filtered back projection method. The tomogram data reconstructed by the computer is stored in the storage device 12 and displayed on the display device 130.

(1) In Embodiment 1, a plurality of radiation detectors 4 are arranged in the radial direction of the through-hole 6 as well as in the axial direction and circumferential direction thereof. Therefore, γ-ray detection signals can be derived from various radial positions of the through-hole 6 without reducing the amount of signal transmission substance although signal transmission substance reduction could not be avoided when radiation detectors for conventional PET examination were used. As a result, Embodiment 1 makes it possible to obtain accurate information about the through-hole section's radial positions reached by γ-rays (the positional information about radiation detectors 4 that output γ-ray detection signals). In the conventional PET examination, one radiation detector is positioned in the radial direction of the through-hole 6, and a reflective material is placed in the radiation detector to acquire the information about the through-hole section's radial positions reached by γ-rays depending on the pattern of signal transmission substance arrival at a photomultiplier. In such an information acquisition process, the signal transmission substance is partly attenuated within the radiation detector or reflected out of the radiation detector due to the inclusion of the reflective material. Therefore, the amount of signal transmission substance decreases to lower the energy resolution.

(2) In Embodiment 1, a plurality of independent radiation detectors 4 are arranged in the radial direction of the through-hole 6. Therefore, the entire signal transmission substance of each radiation detector can be used for γ-ray detection to raise the radiation detector's energy resolution. When radiation detectors having a high-energy resolution are used for the PET examination, γ-rays whose energy is attenuated by scattering can be differentiated from unscattered, 511 keV γ-rays. As a result, an increased amount of scattered radiation can be removed with a filter for the γ-ray discriminator 8.

(3) Embodiment 1 provides a means of acquiring accurate information about the through-hole section's radial positions reached by γ-rays without decreasing the amount of signal transmission substance in radiation detectors. It is therefore possible to increase the tomogram accuracy through the use of accurate information about γ-ray arrival positions and prevent the decrease in the amount of signal transmission substance because the radiation detectors require no reflective material. Thanks to these improvements, the energy resolution increases, thereby minimizing the influence of scattered radiation upon tomogram reconstruction. As a result, Embodiment 1 can increase the tomogram accuracy, that is, the PET examination accuracy.

(4) Embodiment 1 uses semiconductor radiation detectors as the radiation detectors 4. Therefore, a plurality of radiation detectors 4 can be arranged in the radial direction of the through-hole 6 without having to increase the size of the image-pickup device 2.

(5) Embodiment 1 makes it possible to easily locate a faulty radiation detector 4 in a group of radiation detectors 4 by comparing the measured detection efficiency proportion of the radiation detectors 4 with the theoretical detection efficiency proportion of the radiation detectors 4. A faulty radiation detector 4 can easily be located particularly when a plurality of radiation detectors 4 is linearly arranged in the radial direction of the through-hole 6.

(6) In Embodiment 1, an imaging processing can be performed by a single image pickup device 2 so as to compensate for noise caused by detection efficiency difference and noise caused by in-vivo scattered radiation.

In step 47 of Embodiment 1, the tomogram is reconstructed using the corrected PET coefficient that is obtained by correcting the count data, which is corrected in step 45, in accordance with detection efficiency difference in step 46. In an alternative embodiment, however, the count data corrected in step 45 can be used for tomogram reconstruction in step 47 without providing a correction in step 46.

In Embodiment 1, three radiation detectors 4 are linearly arranged in the direction of the radius of the through-hole 6. In an alternative embodiment, however, the second innermost radiation detector 4 can be shifted in the circumferential direction of the through-hole 6 (e.g. so that the second innermost radiation detector is positioned midway between two adjacent innermost radiation detectors) instead of positioning the three radiation detectors linearly. If a plurality of radiation detectors 4 are not linearly arranged in the direction of the radius of the through-hole 6, however, the rate of γ-ray attenuation before γ-ray arrival at the radiation detectors needs to be measured by conducting a test after completion of image pickup device assembly. When a plurality of radiation detectors 4 are linearly arranged in the direction of the radius of the through-hole 6 according to Embodiment 1, such a test need not be conducted because the γ-ray attenuation rates of the radiation detectors 4 are known.

In Embodiment 1, γ-ray in-vivo absorption corrections are made by means of transmission imaging. In an alternative embodiment, however, a common PET correction technique can be used instead of making such corrections. An alternative in-vivo absorption correction method will be described below. The medical examinee 17 is examined by a separately installed X-ray CT apparatus. X-rays passing through the medical examinee 17 are measured by a radiation detector in the X-ray CT apparatus. The rate of attenuation of an X-ray detection signal generated from the radiation detector is used to reconstruct the tomogram of the medical examinee 17 and determine the CT values at various positions within the body of the medical examinee 17. The determined CT values are used to estimate the substance composition at each position within the body of the medical examinee 17. The estimated substance composition data is used to estimate the coefficient of 511 keV linear attenuation at each position. The estimated linear attenuation coefficient data is used by the forward projection method to determine the coefficient of linear attenuation between a pair of semiconductor devices that has detected paired γ-rays during PET examination. The reciprocal of the determined linear attenuation coefficient is multiplied by γ-ray detection signal count data to compensate for a data differential arising out of attenuation within the body.

When the alternative in-vivo absorption correction method described above is used, the calibrated radiation source 31 need not be used.

Embodiment 2

Figure 8:
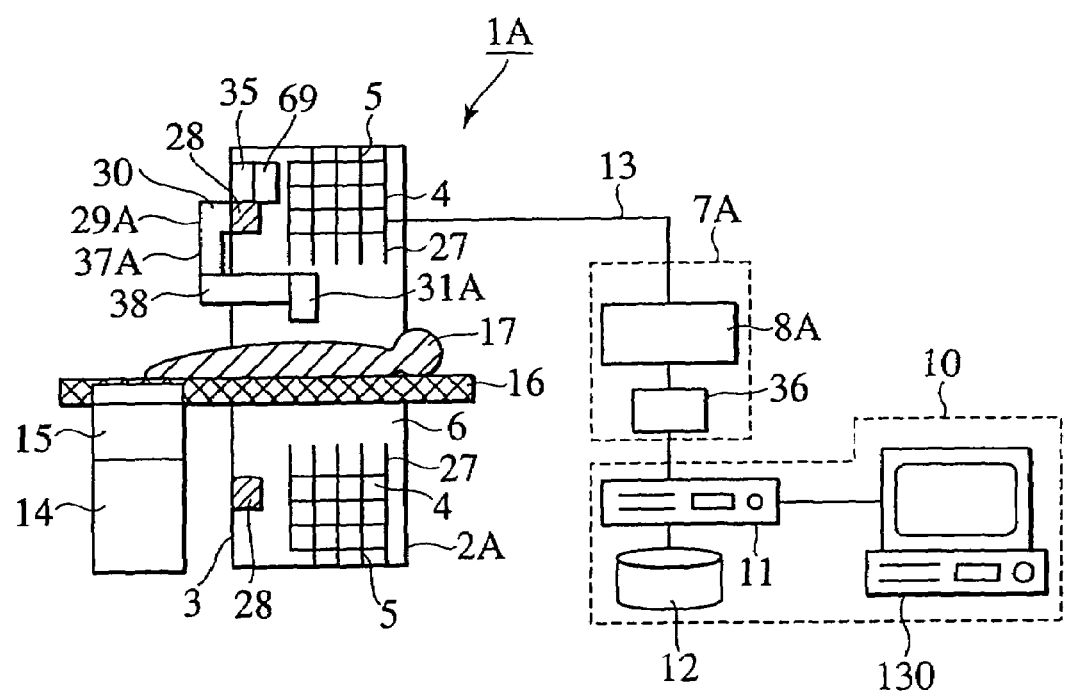
FIG. 8 is a configuration diagram showing a radiological imaging apparatus (SPECT examination apparatus) according to another embodiment of the present invention.

A radiological imaging apparatus of another embodiment (Embodiment 2) of the present invention will be described with reference to FIG. 8. The radiological imaging apparatus 1A of Embodiment 2 is used for SPECT examination. This apparatus 1A comprises an image pickup device 2A in place of the image pickup device 2 for the radiological imaging apparatus 1 and a signal processor 7A instead of the signal processor 7 for the radiological imaging apparatus 1. The other components of the radiological imaging apparatus 1A are the same as for the radiological imaging apparatus 1. The signal processor 7A includes a γ-ray discriminator 8A and a counter 36 connected to the γ-ray discriminator 8A, and is provided for each radiation detector 4. The γ-ray discriminator 8A has a filter energy setting of 120 keV although the filter energy setting for the γ-ray discriminator 8 in Embodiment 1 is 400 keV. The image pickup device 2A differs from the image pickup device 2 in that a collimator 27 is added to the former. Further, the image pickup device 2A uses a calibrated radiation source circumferential transfer unit 37A in place of the calibrated radiation source circumferential transfer unit 37 that is used for the image pickup device 2. The collimator 27 is positioned inside an innermost radiation detector 4 and mounted on a radiation detector support plate 5. The collimator 27, which is circular, absorbs γ-rays that are about to obliquely fall on a radiation detector 4. As is the case with Embodiment 1, Embodiment 2 has a plurality of radiation detector group.

Figure 9A:
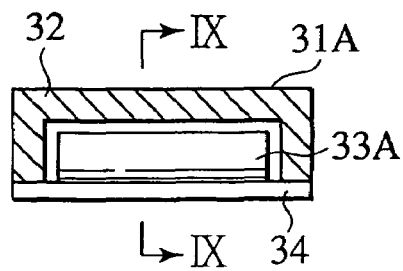
FIG. 9A is a longitudinal sectional view of a calibrated radiation source shown in FIG. 8.
Figure 9B:
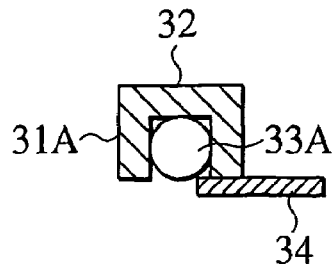
FIG. 9B is a cross sectional view taken along line IX-IX of FIG. 9A.

The calibrated radiation source circumferential transfer unit 37A is provided with a guide rail 28 and a calibrated radiation source device 29A. The calibrated radiation source device 29A includes a calibrated radiation source drive 30, a calibrated radiation source 31A, and an arm 38. The calibrated radiation source 31A is mounted on the arm 38. The calibrated radiation source 31A shown in FIGS. 9A and 9B uses a γ-ray source 33A in place of the γ-ray source 33, which is used for the calibrated radiation source 31, and does not include the collimator 39, which is provided for the calibrated radiation source 31. A radiation source emitting γ-rays of about 141 keV is used as the γ-ray source 33A. For example, 120 keV $^{57}$Co is used.

First of all, transmission data imaging with the radiological imaging apparatus 1A is performed in the same manner as with the radiological imaging apparatus 1 to determine the rate of γ-ray attenuation within the body of a medical examinee. The determined γ-ray attenuation rate is used to compensate for in-vivo scattering during SPECT examination. In Embodiment 2, the radiation detector 4 has an energy of 120 keV.

When the emitted γ-ray energy is uniform, the γ-ray detection efficiency can be determined from a theoretical formula. Since the radiation detectors 4 are semiconductor radiation detectors having a detection unit made of 5 mm thick CdTe, the detection efficiency of 141 keV γ-rays is about 80%. Although Embodiment 2 uses a 120 keV radiation source, appropriate results will be obtained when processing is performed at a setting of 141 keV because the resulting detection efficiency change is insignificant. In a radiation detector group of three layered radiation detectors 4, therefore, incident γ-radiation is attenuated by about 80% in the first layer radiation detector 4, and the 20% γ-radiation passing through the first layer radiation detector 4 is attenuated by about 80% in the second layer radiation detector 4, that is, about 16% γ-radiation attenuation occurs in the second layer radiation detector 4. In the third layer radiation detector 4, the 4% γ-radiation passing through the second layer radiation detector 4 is attenuated by about 80%, that is, about 3.2% γ-radiation attenuation occurs. γ-ray detection signals reflecting such attenuations are output from the radiation detectors 4. When the γ-ray detection signals fed from the layered radiation detectors 4 are independently measured and the measurement result significantly differs (by, for instance, more than ±5%) from the theoretical detection efficiency proportion (80:16:3.2) of the layered radiation detectors 4, it means that one or more of the radiation detectors 4 is deteriorated. As is the case with Embodiment 1, Embodiment 2 also makes it possible to locate a deteriorated radiation detector 4 within a radiation detector group and determine the percentage of detection efficiency decrease caused by deterioration. The concept of fault detection provided by Embodiment 2 will be described below.

In Embodiment 2, γ-rays emitted at a certain time from the γ-ray source 33A fall on three radiation detectors 4 in a radiation detector group due to the shape of the collimator 27, but do not fall on three radiation detectors in a radiation detector group adjacent to the above radiation detector group. However, the concept of fault detection described with reference to Embodiment 1 is still applied to Embodiment 2, and the process applied to Embodiment 2, which will be described later, is virtually the same as that is indicated in FIGS. 5 and 6.

A SPECT examination process performed with the radiological imaging apparatus 1A will be described below. A SPECT pharmaceutical is administered to a medical examinee 17. A bed 16 on which the medical examinee 17 is laid is inserted into a through-hole 6 of an image pickup device 2A. The SPECT pharmaceutical is gathered at a lesion in the medical examinee 17. The lesion in the body of the medical examinee 17 emits 141 keV γ-rays (when the SPECT pharmaceutical contains $^{99}$Tc). Radiation detectors 4 detect the emitted γ-rays as is the case with Embodiment 1. The γ-ray detection signals output from the radiation detectors 4 are received by the associated γ-ray discriminator 8A. The γ-ray discriminator 8A uses a filter to pass a γ-ray detection signal (excluding scattered γ-rays) having energy higher than an energy setting of 120 keV, and generates a pulse signal having an appropriate energy for the γ-ray detection signal. A counter 36 uses the pulse signal to perform counting and determines the count data for the γ-ray detection signal. The counter 36 outputs the count data and the positional information about detection points (positional information about a radiation detector 4 that generated the γ-ray detection signal). A computer 11 associates the count data with the positional information about detection points and stores it in a storage device 12.

The computer 11 uses the count data and other relevant data to perform a processing procedure indicated in FIGS. 5 and 6 to reconstruct a tomogram of the medical examinee 17. Embodiment 2 is different from Embodiment 1 in processing steps 40, 41, 44, 46, and 47, but is equal to Embodiment 2 in the other processing steps. Therefore, the description of Embodiment 2 will cover processing steps 40, 41, 44, 46, and 47 only. In step 40 of Embodiment 2, the count data derived from SPECT examination, the positional information about the associated detection points, and the count data derived from transmission imaging are read from the storage device 12 and input. In step 41, the theoretical detection efficiency proportion of grouped radiation detectors is calculated. This theoretical proportion can be determined by performing theoretical calculations on the transmission distance of γ-rays emitted from the medical examinee 17 (this distance varies with the radionuclides contained in the SPECT pharmaceutical) and the sequence of γ-ray transmission. When a SPECT pharmaceutical containing $^{99}$Tc is administered to the medical examinee 17, the theoretical detection efficiency proportion of the first-layer to third-layer radiation detectors 4 in a radiation detector group is about 80:16:3.2.

In step 44 of Embodiment 2, the attenuation correction count for radiation detectors is calculated. Although paired γ-rays is emitted from a lesion during PET examination, a single γ-ray is emitted during the SPECT examination. Therefore, step 44 of Embodiment 2 differs from the counterpart of Embodiment 1. The attenuation correction count for radiation detectors in a radiation detector group is calculated. As regards the γ-radiation emission from a lesion during SPECT examination, one count data derived from SPECT examination and the γ-ray attenuation rate calculated in step 43 are used to reconstruct the tomogram of the medical examinee 17. First, the transmission image obtained in step 43 is back-projected to determine the γ-ray attenuation rate of each position within the body of the medical examinee 17. The determined γ-ray attenuation rate is used to estimate the substance composition at each position within the body of the medical examinee 17. The estimated substance composition data is used to estimate the coefficient of 141 keV linear attenuation at each position within the body. The estimated linear attenuation coefficient data is used by the forward projection method to determine the average linear attenuation coefficient for cases where γ-rays are generated so that they are incident on a certain radiation detector via the collimator 27. The reciprocal of the determined linear attenuation coefficient is the attenuation correction count.

In step 46 of Embodiment 2, the γ-ray image pickup signal is corrected in accordance with the detection efficiency difference among radiation detectors. In SPECT examination where a single γ-ray is emitted, the count data is corrected using the detection efficiency of a radiation detector group at which the single γ-ray arrives. This correction is made in accordance with equation (2), which is described with reference to Embodiment 1. The value $Xsi_{ij}$ in equation (2) is corrected SPECT count data. The corrected SPECT count data calculated from equation (2) is stored in the storage device 12. In step 47, the tomogram is reconstructed using the corrected SPECT count data $Xsi_{ij}$, which is derived from the correction in step 46, and the positional information about detection points.

Embodiment 2 also provides advantages (1) through (6) of Embodiment 1.

Embodiment 3

A radiological imaging apparatus of another embodiment (Embodiment 3) of the present invention will be described with reference to FIGS. 10 and 11. The radiological imaging apparatus 1B of Embodiment 3 is used for X-ray CT examination (in which an X-ray emission from an X-ray source 60 passes through the body of a medical examinee and is detected by radiation detectors) and PET examination. This apparatus 1B comprises an image pickup device 2B in place of the image pickup device 2 for the radiological imaging apparatus 1 and a signal processor 7A instead of the signal processor 7 for the radiological imaging apparatus 1. The other component's of the radiological imaging apparatus 1B are the same as for the radiological imaging apparatus 1. The image pickup device 2B uses a calibrated radiation source circumferential transfer unit 37B in place of the calibrated radiation source circumferential transfer unit 37 that is used for the image pickup device 2. The calibrated radiation source circumferential transfer unit 37B includes a guide rail 28 and a calibrated radiation source device 29B. The calibrated radiation source device 29B includes a calibrated radiation source drive 30, a calibrated radiation source 31, an X-ray source 60, and an arm 38. The calibration radiation source 31 and X-ray source 60 are mounted on the end of the arm 38. The calibration radiation source 31 and X-ray source 60 may be mounted on the end of the arm 38 so that they are aligned in the circumferential direction of a through-hole 6. The calibrated radiation source circumferential transfer unit 37B doubles as an X-ray source circumferential transfer unit. The calibrated radiation source drive 30 doubles as an X-ray source drive. Embodiment 3 includes a drive controller 35 and a radiation source controller 69.

The X-ray source 60 includes a publicly known X-ray tube, which is not shown. This X-ray tube is provided with an anode, a cathode, a current source for the cathode, and a voltage source for applying a voltage between the anode and cathode, which are mounted inside an external cylinder. The cathode is formed of a tungsten filament. Electrons are emitted from the filament when a current flows from the current source to the cathode. These electrons are accelerated by a voltage (several hundred kV) applied from the voltage source between the cathode and the anode, and collide with the anode (W, Mo, etc.), which is the target. Collision of electrons with the anode produces X-rays of 80 keV. These X-rays are emitted from the X-ray source 60.

Figure 12:
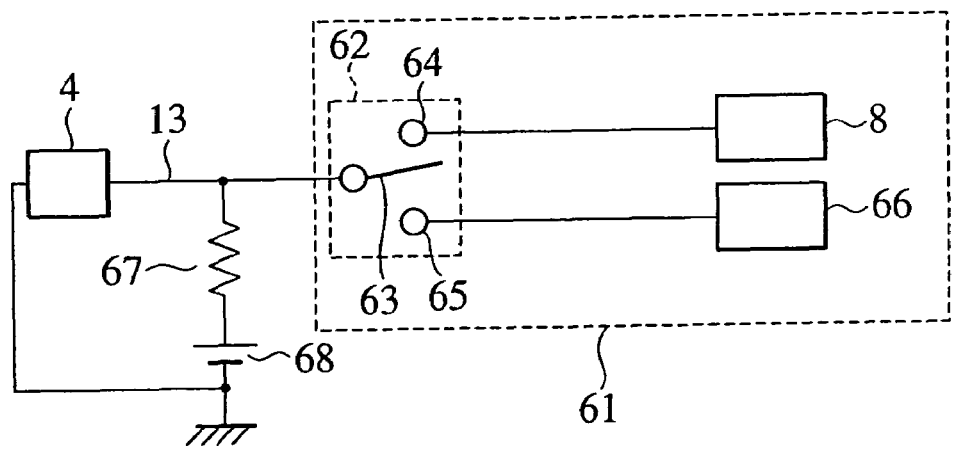
FIG. 12 is a configuration diagram of a signal discriminator shown in FIG. 11.

The signal processor 7A includes a signal discriminator 61, a γ-ray discriminator 8 not included in the signal discriminator 61, and a coincidence counter 9. The signal discriminator 61 is connected to each of the first-layer (4X) radiation detectors 4, which are the innermost radiation detectors in each radiation detector group. As shown in FIG. 12, each of the signal discriminators 61 includes a selector switch 62, a γ-ray discriminator 8, and an X-ray signal processor 66. The selector switch 62 includes a movable terminal 63 and stationary terminals 64 and 65. The first-layer (4X) terminal 63 on the selector switch 62 via a wiring 13. The γ-ray discriminator 8 is connected to the stationary terminal 64, and the X-ray signal processor 66 is connected to the stationary terminal 65. The minus terminal on a power supply 68 is connected to the wiring 13 via a resistor 67. The plus terminal on the power supply 65 is connected to radiation detectors 4. The radiation detectors in the second innermost layer (4Y) and third innermost layer (4Z) within each radiation detector group are connected to their respective γ-ray discriminators 8 as is the case with Embodiment 1. All the γ-ray discriminators 8, including the γ-ray discriminator 8 within the signal discriminator 61, are connected to one coincidence counter 9. The coincidence counter 9 may be furnished for each division of radiation detectors 4 as is the case with Embodiment 1. The coincidence counter 9 and X-ray signal processor 66 are connected to the computer 11.

First, a transmission data imaging process is performed with the calibrated radiation source 31 as is the case with Embodiment 1. After completion of transmission data imaging, the image pickup device 2B is used to conduct a radiological examination (PET examination and X-ray CT examination).

An X-ray CT examination/PET examination process performed according to Embodiment 3 will be described below. A PET pharmaceutical is injected into or otherwise administered to a medical examinee 17 in advance in such a manner that the radioactivity administered to the body of the medical examinee is 370 MBq. When a predetermined period of time elapses, a bed 16, on which the medical examinee 17 is laid, is inserted into the through-hole 6 of the image pickup device 2B so as to position the medical examinee 17 within the through-hole 6. An X-ray CT examination/PET examination is conducted with the image pickup device 2B.

Before giving a detailed description of radiological examination according to Embodiment 3, the principles of radiation detection provided by Embodiment 3 will be described. X-rays emitted from the X-ray source are oriented in a specific direction and incident on the medical examinee for a predetermined period of time, and X-rays passing through the body of the medical examinee are detected by radiation detectors. This X-ray detection operation (scan) is repeated. The data for an X-ray CT image (tomogram that is derived from X-ray CT and contains an image of a medical examinee's internal organs and bones) is created in accordance with the intensity of X-rays detected by a plurality of radiation detectors. For the acquisition of highly accurate X-ray CT image data, it is desirable that γ-rays emitted from the interior of the medical examinee's body due to the administered PET pharmaceutical be not incident on the radiation detectors that are detecting X-rays during X-ray CT examination. The influence of γ-rays on a single radiation detector is negligible when the duration of a medical examinee's exposure to X-rays is shortened in accordance with the rate of γ-ray incidence. Therefore, efforts have been made to reduce the period of time during which the medical examinee is exposed to X-rays. The rate of γ-ray incidence on a radiation detector is considered to determine the duration of X-ray exposure T. When the in-vivo radioactivity based on a PET pharmaceutical to be administered to a medical examinee for PET examination is N (Bq), the rate of generated γ-ray passage through the body of the medical examinee is A, the rate of incidence determined from a solid angle of a radiation detector is B, and the sensitivity of a detection device is C, the rate of γ-ray detection by the radiation detector α (counts/sec) is given by equation (3). In equation (3), the coefficient "2" means that a pair of γ-rays (two γ-rays) are emitted when a positron annihilates.

$$\alpha = 2NABC \quad (3)$$

The probability W with which γ-rays are detected by a detection device within the irradiation time T is given by equation (4).

$$W = 1 - \exp(-T\alpha) \quad (4)$$

When the irradiation time T is determined so as to minimize the value W, the influence of γ-rays incident on a radiation detector during X-ray CT examination is negligible.

A typical X-ray irradiation time T will be described below. The X-ray irradiation time T is determined from equations (3) and (4). The maximum radiation intensity prevailing within the body of a medical examinee due to a PET pharmaceutical administered to the medical examinee for PET examination is about 370 MBq (N=370 MBq). The rate of γ-ray passage through the medical examinee's body A is about 0.6 (A=0.6) on the presumption that the medical examinee's body is water having a radius of 15 cm. If, for instance, 5 mm square radiation detectors are arranged in the form of a ring having a radius of 50 cm, the rate of incidence B determined from the solid angle of one radiation detector is $8 \times 10^{-6}$ (B=$8 \times 10^{6}$). The radiation detector's maximum detection sensitivity C is about 0.6 (C=0.6) when semiconductor radiation detectors are used. These values indicate that the rate of γ-ray detection by one radiation detector α is about 2000 counts/second. If, for instance, the X-ray irradiation time T is 1.5 μsec, the probability W with which a radiation detector detects γ-rays during an X-ray detection processes 0.003. It means that such γ-rays are practically negligible. If the X-ray irradiation time is 1.5 μsec or shorter in situations where the radioactivity administered to the body is 360 MBq or less, W<0.003. It means that the γ-ray detection probability is 0.3% or lower and negligible.

An X-ray CT examination/PET examination performed with the image pickup device 2B according to the above principles will be detailed below.

To start an X-ray CT examination, the drive controller 35 outputs a drive start signal to close a switch (hereinafter referred to as the motor switch) that is connected to a motor for the calibrated radiation source drive 30 and to a power supply. An electrical current is supplied to rotate the motor. The turning force of the motor is transmitted to a pinion via a speed reduction mechanism so that the calibrated radiation source device 29B, that is, the X-ray source 60 circumferentially moves along the guide rail 28. The X-ray source 60 moves around the medical examinee 17 at a preselected speed while it is positioned within the through-hole 6. At the end of the X-ray CT examination, the drive controller 35 outputs a drive stop signal to open the motor switch. This stops the movement of the X-ray source 60 in the circumferential direction. In Embodiment 3, the radiation detectors 4, which are arranged circumferentially in a circular form, do not move in the circumferential direction or in the axial direction of the through-hole 6. For a control signal transmission from the immobile X-ray source controller and drive controller to the mobile X-ray source device, a publicly known technology that does not obstruct the movement of the X-ray source device is used.

The radiation source controller 69 controls the time of X-ray emission from the X-ray source 60. More specifically, the radiation source controller 69 repeatedly outputs an X-ray generation signal and X-ray shut-off signal. The first X-ray generation signal is output in accordance with the input of the above drive start signal to the radiation source controller 69. Upon X-ray generation signal output, a switch (this switch is hereinafter referred to as the X-ray source switch; not shown) provided between the X-ray tube anode (or cathode) of the X-ray source 60 and power supply closes. When a first preselected period of time elapses, the X-ray shut-off signal is output to open the X-ray source switch. When a second preselected period of time elapses, the X-ray source switch closes. Radiation source control is repeatedly exercised in this manner. For the first preselected period of time, a voltage is applied between the anode and cathode. For the second preselected period of time, however, such a voltage application does not take place. Thanks to the control exercised by the radiation source controller 69, the X-ray tube emits 80 keV X-rays in a pulsating manner. The irradiation time T, which is the first preselected period of time, is set, for instance, to 1 μsec so that the γ-ray detection probability at radiation detectors 4 can be neglected. The second preselected period of time is the time interval T0 during which the X-ray source 60 moves from one radiation detector 4 to a circumferentially adjacent radiation detector 4, and determined by the speed at which the X-ray source 60 moves circumferentially on the guide rail 28. The first and second preselected periods of time are stored in the radiation source controller 69.

When the X-ray shut-off signal and X-ray generation signal are repeatedly output, the X-ray source 60 emits X-rays for the first preselected period of time, that is, 1 μsec, and halts its X-ray emission for the second preselected period of time. This X-ray emission and shut-off cycle is repeated while the X-ray source 60 moves in the circumferential direction.

X-rays emitted from the X-ray source 60 fall on the medical examinee 17 in the form of a fan beam. As the X-ray source 60 moves in the circumferential direction, X-rays come from the circumference to fall on the medical examinee 17. X-rays passing through the medical examinee 17 are detected by a plurality of radiation detectors 4 circumferentially positioned around a radiation detector 4 that is mounted 180 degrees away from the X-ray source 60 when the axial center of the through-hole 6 is regarded as the base point. These radiation detectors output the detection signals related to the detected X-rays. The X-ray detection signals are then entered in the respective signal discriminators 61 via the associated wirings 13. These X-ray detecting radiation detectors 4 are referred to as first radiation detectors 4 for the sake of convenience.

From the medical examinee 17 on the bed 16, 511 keV γ-rays are emitted due to the administered PET pharmaceutical. Radiation detectors 4 other than the first radiation detectors 4 output γ-ray detection signals. These γ-ray detecting radiation detectors 4 are referred to as second radiation detectors 4 for the sake of convenience. The γ-ray detection signals output from the second radiation detectors in the first layer are delivered to the respective signal discriminators 61 via the associated wirings 13. The γ-ray detection signals output from the second radiation detectors in the second and third layers are delivered to the respective γ-ray discriminators 8 via the wirings 13. Note that only the radiation detectors 4 in the first layer are connected to the signal discriminators 61. The reason is that almost all X-rays (more than 90%) passing through the medical examinee 17 are detected by the radiation detectors 4 in the first layer since the X-ray energy is 80 keV.

Within the signal discriminator 61, the γ-ray detection signal output from a second radiation detector 4 in the first layer is conveyed to a γ-ray discriminator 8, and the X-ray detection signal output from a first radiation detector 4 is conveyed to the X-ray signal processor 66. These detection signal transmission operations are performed in accordance with a switching operation of the selector switch 62 of the signal discriminator 61. The switching operation for connecting the movable terminal 63 of the selector switch to the stationary terminal 64 or 65 is performed in accordance with a switching control signal that is output from the drive controller 35. The drive controller 35 selects the first radiation detector 4 from the radiation detectors 4 in the first layer, and connects the movable terminal 63 to the stationary terminal 65 in the signal discriminator 61 to be connected to the first radiation detector 4. The theoretical detection efficiency proportion of three layered radiation detectors in a radiation detector group is 20:16:12.8 (the values are arranged in order from the innermost detector to the outermost).

The selection of the first radiation detectors 4 will be described. An encoder (not shown) is linked to a motor in the calibrated radiation source drive 30. The drive controller 35 inputs the encoder's detection signal, determines the circumferential position of the calibrated radiation source drive 30, that is, the X-ray source 60, and uses the stored positional data about radiation detectors 4 to select a radiation detector 4 that is positioned 180° away from the X-ray source 60. Since the X-rays emitted from the X-ray source 60 has a width in the circumferential direction of the guide rail 28, not only the selected radiation detector 4 but also the other radiation detectors positioned in the circumferential direction detect X-rays passing through the medical examinee 17. The drive controller 35 selects such additional radiation detectors as well. These radiation detectors are the first radiation detectors. As the X-ray source moves in the circumferential direction, the first radiation detectors 4 change. It looks as if the first radiation detectors 4 moved in the circumferential direction during the circumferential travel of the X-ray source 60. When the drive controller 35 selects another radiation detector 4 during the circumferential travel of the X-ray source 60, the movable terminal 63 connected to the newly designated first radiation detector 4 is connected to stationary terminal 65. When the movable terminal 63 is connected to a radiation detector 4 that is no longer the first radiation detector 4 due to the circumferential travel of the X-ray source 60, it is connected to the stationary terminal 64 by the drive controller 35. A radiation detector in the first layer becomes a first radiation detector 4 at a certain time and becomes a second radiation detector 4 at another time, depending on the positional relationship to the X-ray source 60. Therefore, a radiation detector 4 in the first layer outputs both an X-ray image pickup signal and a γ-ray image pickup signal at different times.

A first radiation detector 4 detects X-rays passing through the medical examinee 17 after being emitted from the X-ray source 60 for a first preselected period of time, that is, 1 μsec. The probability with which the first radiation detector 4 detects a γ-ray emission from the medical examinee 17 for a 1 μsec period is very low and negligible as explained earlier. Many γ-rays generating within the body of the medical examinee 17 due to the administered PET pharmaceutical are not emitted in a specific direction but emitted in all directions. As described earlier, these γ-rays are paired, emitted in almost opposite directions (180°±0.6°), and detected by a certain second radiation detector 4.

A signal process performed by a signal discriminator 61 when it receives an X-ray detection signal/γ-ray detection signal output from a radiation detector 4 in the first layer will be described. As explained earlier, the X-ray detection signal output from a first radiation detector 4 is received by the X-ray signal processor 66 via the selector switch 62. The X-ray signal processor 66 uses an integrator to perform calculations on the input X-ray detection signal and outputs the information about the integrated X-ray detection signal value, that is, the measured X-ray intensity. The intensity information about the X-ray detection signal is conveyed to the computer 11 and stored in the storage device 12 by the computer 11. The γ-ray detection signal output from a second radiation detector 4 in the first layer is received by a γ-ray discriminator 8 via the selector switch 62. The γ-ray discriminator 8 for a signal discriminator 61 generates a pulse signal having a predetermined energy when it receives a γ-ray detection signal having an energy greater than an energy setting (400 keV). As is the case with Embodiment 1, a coincidence counter 9 receives pulse signals output from all γ-ray discriminators 8, and outputs the count data about each γ-ray detection signal and the positional information about the two points of paired γ-ray detection. The count data and positional information are conveyed to the computer 11 and stored in the storage device 12 by the computer 11.

The computer 11 performs a process indicated in FIG. 13. The X-ray detection signal intensity, the count data and positional information about the associated detection points derived from PET examination, and the count data derived from transmission data imaging are read from the storage device 12 and input (step 69). The rate of X-ray attenuation in each voxel within the body of the medical examinee 17 is calculated from the X-ray detection signal intensity (step 70). The calculated X-ray attenuation rate is stored in the storage device 12. The tomogram of the medical examinee 17 is reconstructed using the rate of X-ray detection signal attenuation at the associated positions (step 71). The tomogram reconstructed using the X-ray detection signal attenuation rate is referred to as an X-ray CT image. For X-ray CT image reconstruction purposes, the X-ray detection signal attenuation rate read from the storage device 12 is used to determine the coefficient of linear attenuation within the body of the medical examinee 17 between the X-ray source 60 and the semiconductor device unit of a first radiation detector 4. This linear attenuation coefficient is used to determine the linear attenuation coefficient of each voxel by the filtered back projection method. The linear attenuation coefficient of each voxel is used to determine the CT value of each voxel. The determined voxel CT values are used to obtain X-ray CT image data. The X-ray CT image data is stored in the storage device 12. Next, the cross-sectional tomogram of the medical examinee 17 is reconstructed using the γ-ray detection signal count data about the associated positions and the positional information about detection points (step 72). The tomogram reconstructed using the γ-ray detection signal count data is referred to as a PET image. In step 72, processing steps 41 through 47 in FIG. 5, which is used for the description of Embodiment 1, are performed to obtain a PET image. The obtained PET image data is stored in the storage device 12. The PET image data and X-ray CT image data are synthesized to obtain synthesized tomogram data, which contains both the PET image data and X-ray CT image data. The resulting synthesized tomogram data is stored in the storage device 12 (step 73). Synthesis of PET image data and X-ray CT image data can be achieved easily and accurately by aligning a reference point common to these two image data (e.g., central axis position of the through-hole 6). Positional alignment can be accurately achieved because the PET image data and X-ray CT image data are generated according to detection signals output from shared radiation detectors 4. The synthesized tomogram data is recalled from the storage device 12, output to the display device 130 (step 74), and displayed on the display device 130. Since the synthesized tomogram displayed on the display device 130 contains an X-ray CT image, a diseased area visualized by a PET image can easily be located within the body of a medical examinee 17. More specifically, since the X-ray CT image contains an image of internal organs and bones, doctors can locate a diseased area (e.g., cancerous area) based on the relationship to the internal organs and bones.

Embodiment 3 provides the following advantages in addition to advantages (1) through (6) of Embodiment 1.

(7) In Embodiment 3, it is possible to detect not only a plurality of paired γ-rays emitted from a medical examinee 17 or a subject with radiation detectors 4 arranged around the circumference of the through-hole 6 but also X-rays that are emitted from a circumferentially moving X-ray source 60 and passed through the medical examinee 17 (with radiation detectors 4 in the first layer). Although a conventional technology required the use of an image pickup device for detecting transmitted X-rays and the use of another image pickup device for detecting γ-rays, Embodiment 3 requires the use of only one image pickup device and simplifies the structure of a radiological imaging apparatus that provides both X-ray CT examinations and PET examinations.

(8) In Embodiment 3, each of first-layer radiation detectors 4 arranged around the circumference of the through-hole 6 outputs both an X-ray detection signal and γ-ray detection signal. This configuration contributes toward radiological imaging apparatus structure simplification and downsizing.

(9) Embodiment 3 uses X-ray detection signals output from radiation detectors 4 in the first layer to reconstruct a first tomogram (X-ray CT image) of a medical examinee 17, which contains an image of internal organs and bones. It also uses γ-ray detection signals output from radiation detectors 4 in the first to third layers to reconstruct a second tomogram (PET image) of the medical examinee 17, which contains an image of a diseased area. Since first and second tomogram data are reconstructed in accordance with the signals output from radiation detectors 4 that are mounted around the circumference of the through-hole 6 in an image pickup device 2B, the first and second tomogram data can be synthesized with their positional relationship accurately adjusted. Therefore, an accurate tomogram (synthesized tomogram) containing an image of a diseased area, internal organs, and bones can be obtained with ease. The resulting synthesized tomogram makes it possible to accurately locate a diseased area based on the relationship to the internal organs and bones. The first and second tomogram data can easily be synthesized by, for instance, effecting tomogram alignment with respect to the axial center of the through-hole 6 in the image pickup device 2B.

(10) In Embodiment 3, detection signals necessary for the creation of a first tomogram and detection signals necessary for the creation of a second tomogram can be obtained from shared radiation detectors 4. Therefore, the time required for the examination of a medical examinee 17 (examination time) can be considerably reduced. In other words, the detection signals necessary for the creation of the first tomogram and the detection signals necessary for the creation of the second tomogram can be obtained within a short examination time. Unlike a conventional technology, Embodiment 3 minimizes the probability with which a medical examinee moves because it does not have to transfer a medical examinee from an image pickup device for transmitted X-ray detection to another image pickup device for γ-ray detection. Since the necessity for transferring a medical examinee from an image pickup device for transmitted X-ray detection to another image pickup device for γ-ray detection is eliminated, the time required for the examination of a medical examinee can be reduced.

(11) Since the amount of γ-ray image pickup signal input to the X-ray signal processor 66, that is, a first signal processor is considerably reduced, accurate data about a first tomogram can be obtained. Therefore, when image data derived from the synthesis of the data about a first tomogram and the data about a second tomogram is used, diseased areas can be located with increased accuracy.

(12) In Embodiment 3, the X-ray source 60 circulates inside a number of arrayed radiation detectors. Therefore, the diameter of the through-hole 6 increases, making it possible to increase the number of radiation detectors 4 to be mounted in the first layer. Increasing the number of radiation detectors 4 mounted in the circumferential direction enhances the sensitivity and improves the cross-sectional image resolution of a medical examinee 17.

(13) In Embodiment 3, the arm 38 on which the X-ray source 60 is mounted and the X-ray source 60 are positioned inside radiation detectors 4. Therefore, they could obstruct the γ-rays emitted from a medical examinee 17 and prevent radiation detectors 4 positioned immediately behind them from detecting such γ-rays, resulting in the loss of detected data necessary for PET image formation. In Embodiment 3, however, the calibrated radiation source drive 30 rotates the X-ray source 60 and arm 38 in the circumferential direction as described earlier. Therefore, Embodiment 3 does not incur any substantial loss of data. It should be noted in this connection that the X-ray source 60 and arm 38 rotate at a rate of about 1 second per slice. The time required for the rotation of the X-ray source and arm is considerably shorter than the minimum time required for PET examination, which is on the order of several minutes. It means that no substantial data loss can occur.

Embodiment 4

Figure 14:
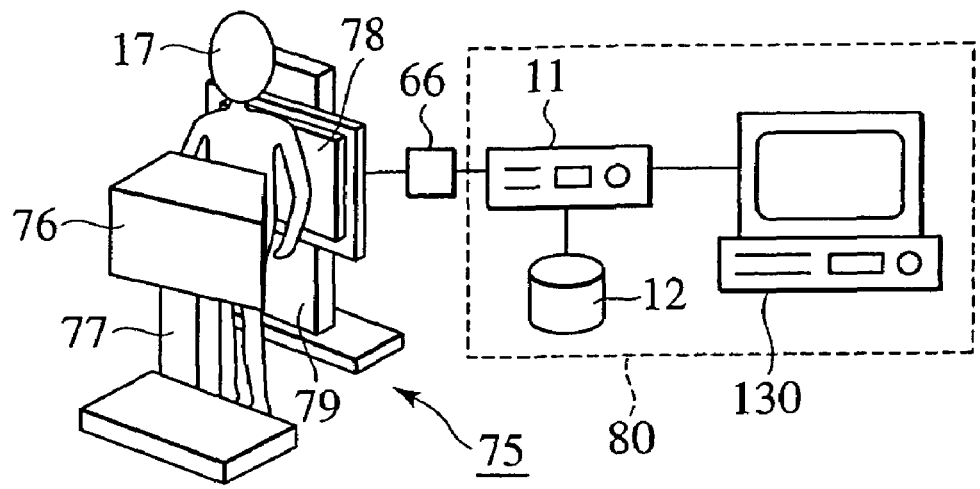
FIG. 14 is a configuration diagram showing a radiological imaging apparatus according to another embodiment of the present invention.
Figure 15:
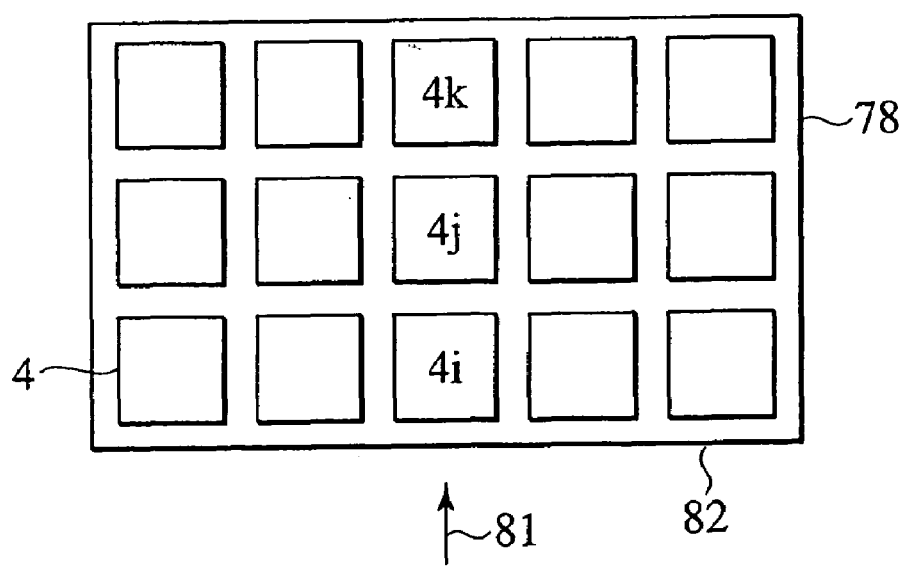
FIG. 15 is a diagram illustrating a typical radiation detector arrangement for a flat panel display shown in FIG. 14.

A radiological imaging apparatus of another embodiment (Embodiment 4) of the present invention will be described with reference to FIG. 14. The radiological imaging apparatus 75 of Embodiment 4 is a digital X-ray examination apparatus that uses a flat panel detector. The radiological imaging apparatus 75 includes an X-ray source 76 that is supported by a stanchion 77, a flat panel detector provided with a plurality of radiation detectors (not shown) and supported by a stanchion 79, X-ray signal processors 66, and an X-ray imaging device 80. Within the flat panel detector 78, a large number of radiation detectors 4 are arranged in the direction of the height and in the direction of the width. As indicated by radiation detectors 4i, 4j, and 4k in FIG. 15, the radiation detectors 4 are also linearly arranged in the direction of the depth (in the traveling direction of X-rays passing through a medical examinee 17) so as to form three layers of radiation detectors. A plane 82 shown in FIG. 15 faces the X-ray source 76. The X-ray signal processor 66 is connected to the radiation detectors 4. The X-ray imaging device 80 includes a computer 11, a storage device 12, and a display device 130. The storage device 12 and display device 130 are connected to the computer 11 to which all the radiation detectors are connected.

An X-ray examination performed with the radiological imaging apparatus 75 will be described below. A medical examinee 17 stands between the X-ray source 76 and flat panel detector 78 with its back facing the X-ray source 76. X-rays emitted from the X-ray source 76 pass through the medical examinee 17 and are detected by the radiation detectors 4 in the flat panel detector 78. The radiation detectors 4 detect X-rays and output X-ray detection signals. The X-ray signal processors 66 add up the X-ray detection signals so as to output the information about X-ray intensity. The X-ray intensity information output from each X-ray signal processor 66 is entered in the computer 11 and stored in the storage device 12. The computer 11 acquires the X-ray intensity information from the storage device 12 and calculates the rates of X-ray attenuation at various positions within the body of the medical examinee 17.

A radiation detector group is formed by three layered radiation detectors 4 that are linearly arranged in the direction of the depth, beginning with the plane 82 of the flat panel detector 78. In Embodiment 4, the detection efficiency proportion of radiation detectors 4 in a radiation detector group also varies with the energy of X-rays emitted from the X-ray source 76. When, for instance, the radiation detectors 4 having a detection unit, which is a 2 mm cube made of CdTe, detect 100 keV rays passing through a medical examinee 17, the theoretical detection efficiency proportion prevailing within the radiation detector group is about 84:13:2.5. This theoretical detection efficiency proportion is stored in the storage device 12.

The computer 11 uses the X-ray intensity information stored in the storage device 12 to calculate the measured detection efficiency proportion of radiation detectors 4 in each radiation detector group. The computer 11 performs processing step 52 of Embodiment 1. When the deviation of the calculated measured detection efficiency proportions from the theoretical one is within a predefined range, the computer 11 uses the above-calculated X-ray attenuation rate to generate grayscale image data for X-ray imaging of the medical examinee 17. If the above-mentioned deviation is outside the predefined range, on the other hand, the computer 11 performs processing steps 53, 54, and 55 of Embodiment 1. When the detection efficiency of a deteriorated radiation detector is corrected in processing step 55, the X-ray intensity for that radiation detector is determined according to the corrected detection efficiency, and the above-mentioned X-ray attenuation rate is corrected with the determined X-ray intensity taken into account. The computer 11 uses the corrected X-ray attenuation rate to generate the above-mentioned grayscale image data.

Embodiment 4 provides advantages (1) through (5) of Embodiment 1. However, it should be noted that advantage (3) results in an increase in the X-ray image accuracy.

In Embodiment 4, the radiation detectors do not always have to be linearly arranged in the direction of the depth of the flat panel detector 78. They can be alternatively arranged so that all the radiation detectors 4 in the second layer overlap with two radiation detectors in the first layer (as viewed from the plane 82).

Next, the correction method to be used when the radiation detectors are not linearly arranged will be described with reference to an example in which a flat panel detector is used for digital X-ray examination. Although a radiological imaging apparatus having a flat panel detector is the same as indicated in FIG. 10, the first- to third-layer radiation detectors 4 for the flat panel detector 70 are nonlinearly arranged with the second-layer radiation detectors 4 shown in FIG. 15 displaced laterally. Even when the radiation detectors 4 are arranged in this manner to form multiple layers, it is possible to locate part of deteriorated radiation detectors 4 and provide corrections for the measured values of deteriorated radiation detectors.

Embodiment 5

Figure 16:
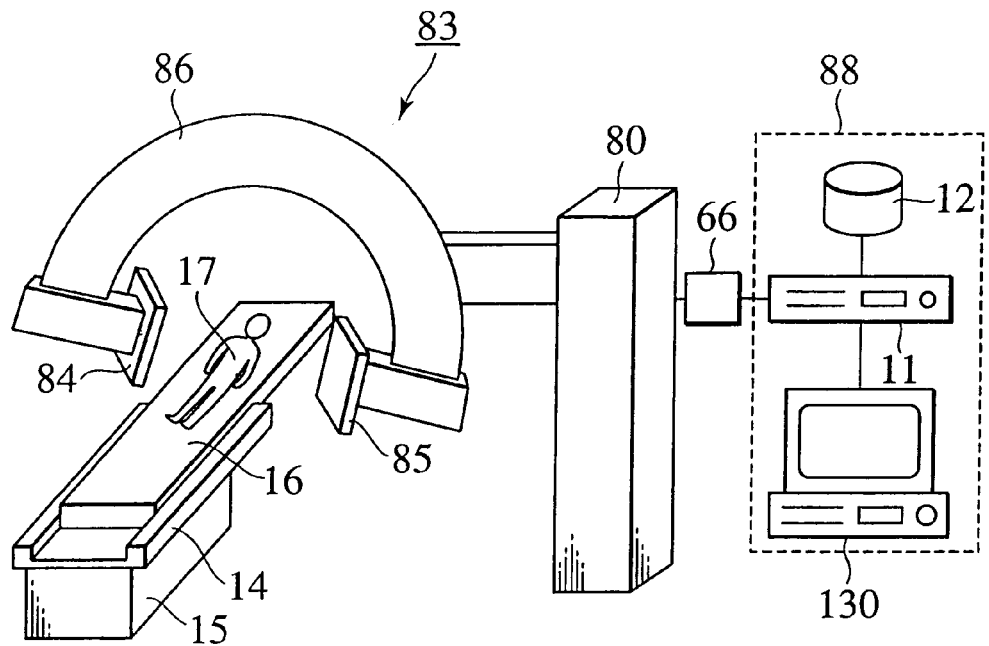
FIG. 16 is a configuration diagram showing a radiological imaging apparatus according to another embodiment of the present invention.
Figure 17:
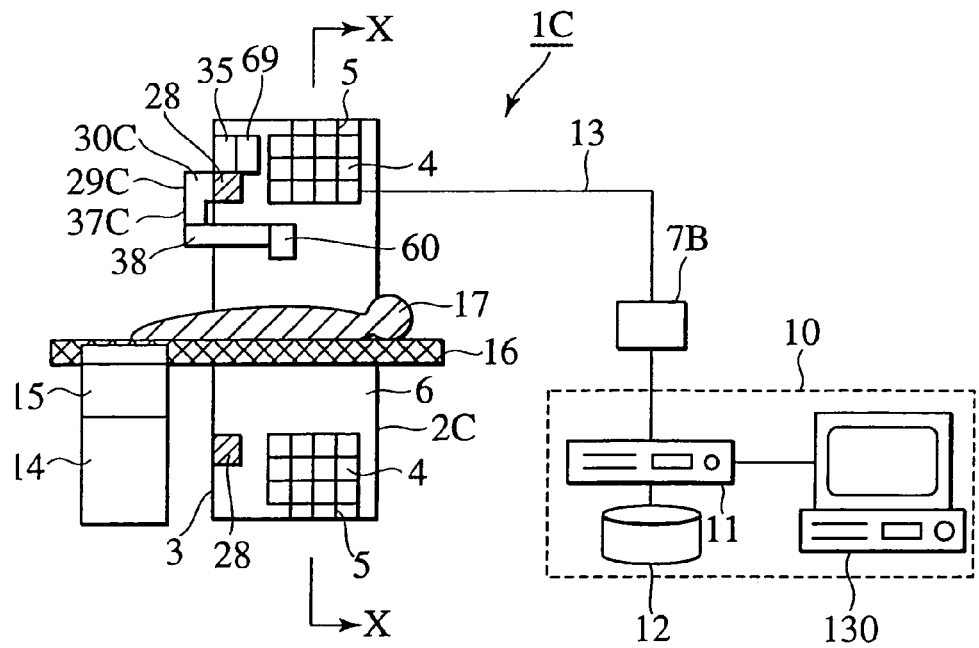
FIG. 17 is a configuration diagram showing a radiological imaging apparatus according to another embodiment of the present invention.

A radiological imaging apparatus of another embodiment (Embodiment 5) of the present invention will be described with reference to FIG. 16. The radiological imaging apparatus 83 of Embodiment 5 is an X-ray CT apparatus. The radiological imaging apparatus 83 includes an X-ray source 84 that is mounted on an arm 86, a radiation detector unit 85 mounted on the arm 86, X-ray signal processors 66, and a tomogram generator 88. The arm 86 is supported by a stanchion 87. The X-ray source 84 and radiation detector unit 85 face each other and are positioned away from each other so that a medical examinee 17 can be positioned between them. As is the case with the flat panel detector 78, the radiation detector unit 85 is equipped with a large number of radiation detectors 4. The radiation detectors 4 are not only arranged in the direction of the height and in the direction of the width, but also linearly arranged in the direction of the depth, beginning with the plane facing the X-ray source 84, so as to form three radiation detection layers. The arm 86 can be rotated, although the details of its mechanism are not shown, so that the X-ray source 84 and radiation detector unit 85 move around the medical examinee 17 lying on a bed 16.

An examination performed with the radiological imaging apparatus 83 will be described below. A medical examinee 17 lying on the bed is positioned between the X-ray source 84 and radiation detector unit 85. X-rays emitted from the X-ray source 84 fall on the medical examinee 17 and pass through the body of the medical examinee 17. The X-rays transmitted in this manner are detected by the radiation detectors 4 in the radiation detector unit 85. The rotating device (not shown) for the arm 86 rotates the X-ray source 84 and radiation detector unit 85 around the medical examinee 17 (through 180° or 360° relative to a certain cross section of the medical examinee 17). X-ray detection signals output from the radiation detectors 4 are entered in the respective X-ray signal processors 66. The X-ray signal processors 66 determine the X-ray intensity in accordance with the measurements of the X-ray detection signals. In accordance with the X-ray intensity, a computer 11 calculates the medical examinee's in-vivo X-ray attenuation rate that prevails between the rotating X-ray source 84 and the portion of the rotating radiation detector unit 85 that faces the X-ray source 84. The linear attenuation coefficient determined in this manner is stored in the storage device 12.

In the same manner as in step 51 of Embodiment 1, the computer 11 calculates the detection efficiency proportion of three layered radiation detectors 4 that are linearly arranged beginning with the plane facing the X-ray source 84 for the radiation detector unit 85, and then continues to perform processing steps 52, 53, 54, and 55 of Embodiment 1. When the deviation of the calculated measured detection efficiency proportion from the theoretical one is found in processing step 52 to be within a predefined range, the computer 11 uses the aforementioned filtered back projection method or the like to determine the linear attenuation coefficient of each voxel from the detector-to-radiation source X-ray attenuation rate stored in the storage device 12, and converts the resulting value to a CT value. If the above deviation is found in processing step 52 to be outside the predefined range, on the other hand, the computer 11 uses the corrected detection efficiency value to correct the linear attenuation coefficient stored in the storage device 12, and calculates the CT value from the corrected linear attenuation coefficient. The computer 11 uses the CT value of each voxel to reconstruct the X-ray CT image.

Embodiment 5 provides the advantages of Embodiment 4.

Embodiment 6

When γ-rays emitted from a medical examinee due to an administered PET pharmaceutical fall on a radiation detector, they attenuate although in some cases they may pass through as they are. When γ-ray attenuation occurs within a radiation detector, the radiation detector outputs a detection signal (electrical charge) that corresponds to the γ-ray energy attenuation. Detected (attenuated) γ-rays scatter within the radiation detector except when they suffer total attenuation. Scattered γ-rays change their direction of travel and fall on another radiation detector at a different angle of incidence. It goes without saying that scattered γ-rays may pass through a radiation detector without suffering any subsequent attenuation, suffer total attenuation within another radiation detector, or scatter again and become detected. In other words, γ-rays detected by a radiation detector may be either unscattered γ-rays (not scattered by a radiation detector) or scattered γ-rays.

As described above, γ-rays change the direction of their travel when they scatter. Therefore, the source of γ-ray generation does not exist on the extension of a scattered γ-ray vector. That is, PET image data based on scattered γ-ray detection signals turns out to be erroneous, causing an error. In consideration of energy attenuation upon γ-ray scattering, therefore, γ-rays having an energy smaller than a predefined threshold energy value were conventionally considered to be scattered and then removed. When such a method was employed, however, unscattered γ-rays were frequently regarded as scattered γ-rays simply because their energy was below the above-mentioned threshold energy value so that the PET image data collection efficiency was lowered.

A nuclear medicine diagnostic apparatus described in JP-A No. 321357/2000 subjects γ-ray detection signals to coincidence counting when it detects a plurality of γ-rays, concludes that nearly simultaneously detected γ-rays are generated from the same source, checks whether the calculated total energy of the detected γ-rays is within a predefined range, and determines whether unscattered γ-rays are included in the detected γ-rays. When it concludes that unscattered γ-rays are included, it selects an initial γ-ray incidence position by picking up one detected γ-ray having a statistically high probability of being unscattered. However, the initial incidence position determined by this conventional technology is selected probabilistically and may be in error. Therefore, this conventional technology merely provides a limited increase in the detection.

As a solution to the problem with the nuclear medicine diagnostic apparatus described in JP-A No. 321357/2000, a radiological imaging apparatus of another embodiment (Embodiment 6) of the present invention will be described with reference to FIGS. 17 through 22. The radiological imaging apparatus 1C of Embodiment 6 aims at locating unscattered γ-rays with high efficiency and generating highly accurate PET images.

Figure 10:
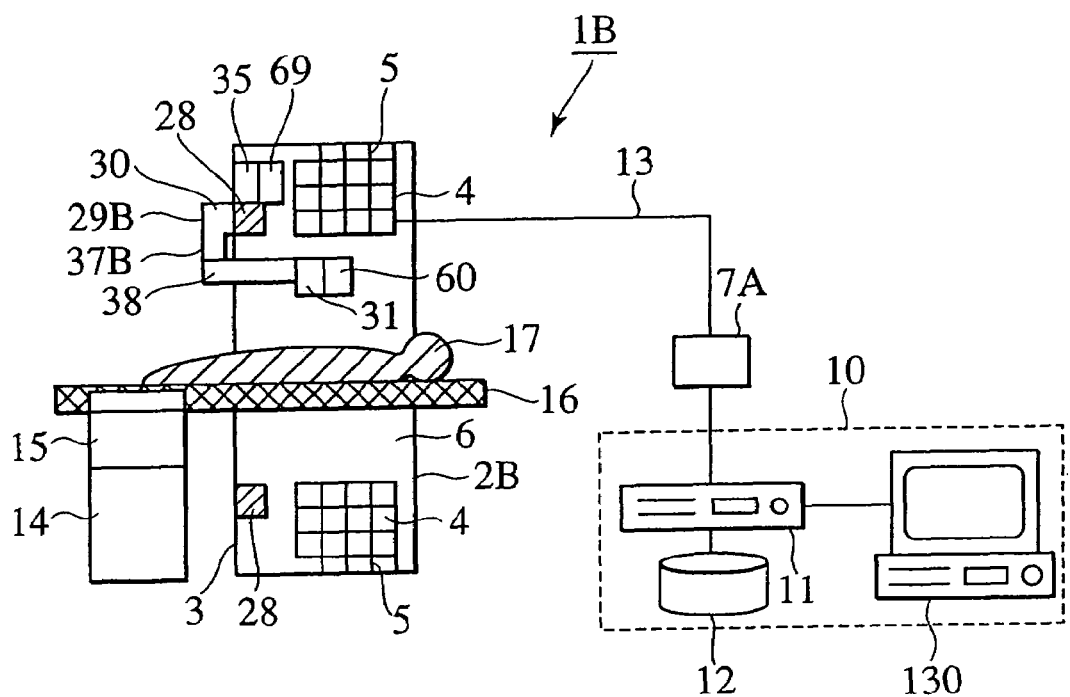
FIG. 10 is a configuration diagram showing a radiological imaging apparatus according to another embodiment of the present invention.
Figure 11:
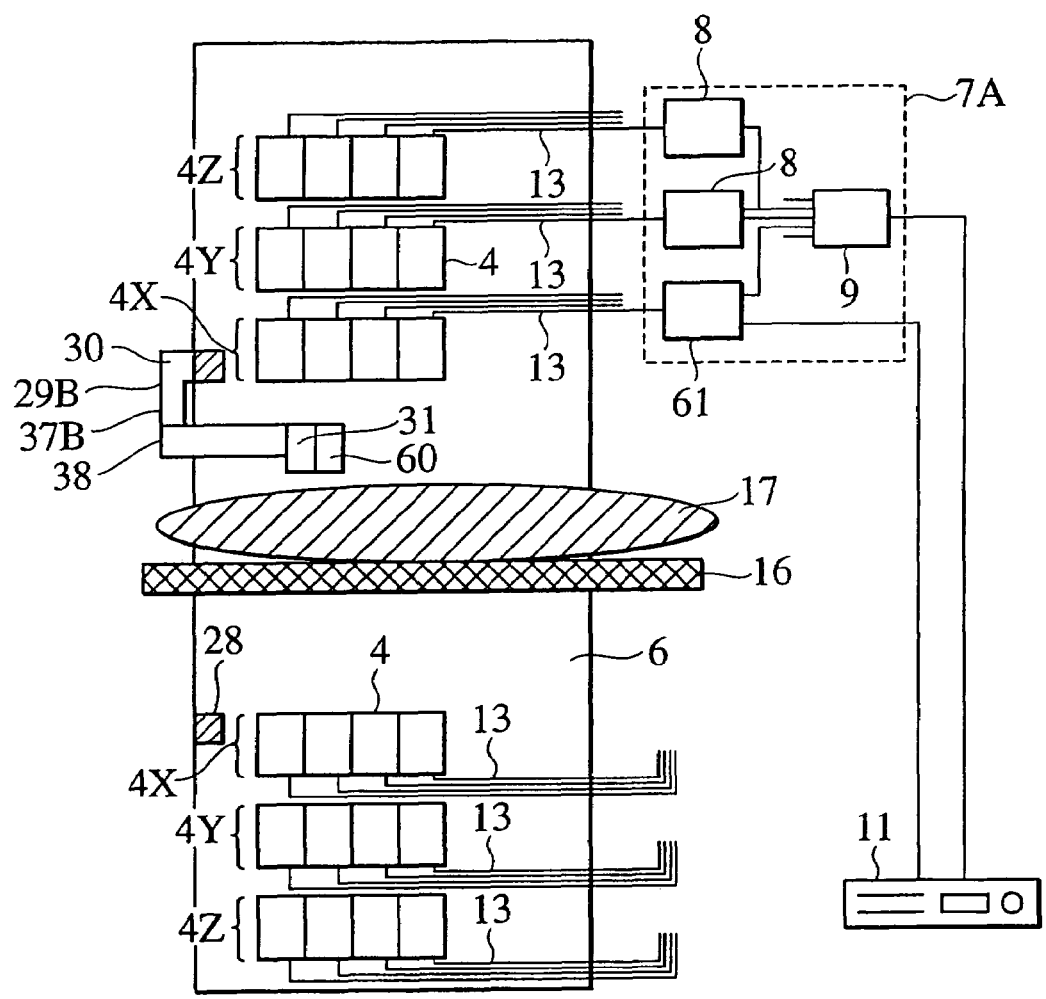
FIG. 11 is a diagram illustrating a radiation detector-to-signal processor connection according to the embodiment shown in FIG. 10.
Figure 18:
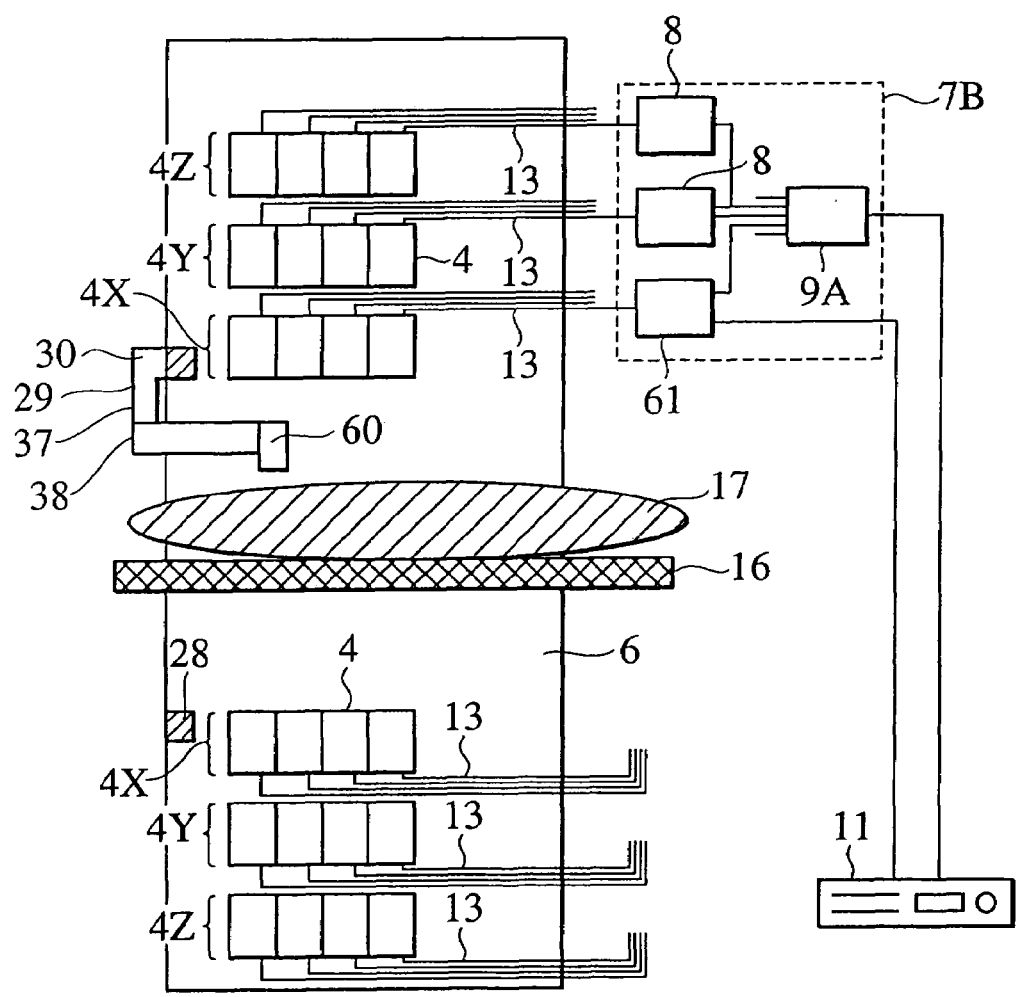
FIG. 18 is a diagram illustrating a radiation detector-to-signal processor connection according to the embodiment shown in FIG. 17.
Figure 19:
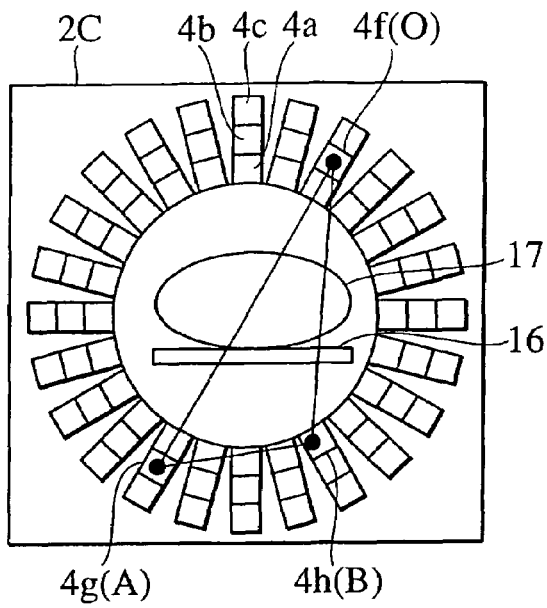
FIG. 19 is a cross sectional view taken along line X-X of FIG. 17.

The radiological imaging apparatus 1C employs the same hardware configuration as the radiological imaging apparatus 1B shown in FIG. 10, except that the former uses an image pickup device 2C in place of the image pickup device 2B and a signal processor 7B in place of the signal processor 7A. The image pickup device 2C has the same configuration as the image pickup device 2B, except that the former uses an X-ray source circumferential transfer unit 37C in place of the calibrated radiation source circumferential transfer unit 37B and does not contain the calibrated radiation source 31. The other components of the image pickup device 2C are the same as those of the image pickup device 2B. The X-ray source circumferential transfer unit 37C includes an X-ray source drive 30C, an X-ray source device 29C that is provided with an arm 38 and an X-ray source 60, and a guide rail 28. The X-ray source drive 30C has the same configuration as the calibrated radiation source drive 30. The X-ray source 60 has the same configuration as the counterpart of Embodiment 3. The signal processor 7B has the same configuration as the signal processor 7A, except that the former uses a coincidence counter 9A in place of the coincidence counter 9 as shown in FIG. 18. The radiological imaging apparatus 1C includes a drive controller 35 and a radiation source controller 69. Sets of three layered radiation detectors 4 are arranged in the direction of the radius of a through-hole 6 as shown in FIG. 19 and mounted on a radiation detector support plate 5 as shown in FIG. 3.

After the administration of a PET pharmaceutical, a bed 16 on which a medical examinee 17 lies is moved to position the medical examinee 17 within the through-hole 6. At the beginning of an X-ray CT examination, the drive controller 35 closes a motor switch. When the motor switch closes, a power source supplies an electrical current to the motor (mounted in the X-ray source drive 30C) so that the X-ray source device 29C rotates around the medical examinee 17. As is the case with Embodiment 3, the drive controller 35 also exercises switching control of a selector switch 62 (shown in FIG. 12), which is provided for a signal discriminator 61. As is the case with Embodiment 3, the radiation source controller 69 exercises open/close control over an X-ray source switch connected to an X-ray tube of the X-ray source 60 during an X-ray CT examination for the purpose of allowing the X-ray source 60 to emit X-rays (8:0 keV) for a first preselected period of time (e.g., 1 μsec) and inhibiting the X-ray source 60 from emitting X-rays for a second preselected period of time. As a result, X-rays come from the circumference to fall on the medical examinee 17.

After X-rays pass through the medical examinee 17, they are detected by a plurality of first radiation detectors 4 that exist within a predefined area facing nearly the X-ray source 60, which is on the opposite side of the through-hole 6. X-ray detection signals output from the first radiation detectors 4 (contained in a row of first-layer detectors 4X) are conveyed via a wiring 13 and a selector switch 62.

Meanwhile, γ-rays emitted from the body of the medical examinee 17 due to PET pharmaceutical administration are detected by second radiation detectors 4 in detector row 4X and radiation detectors 4 in second-layer detector row 4Y and third-layer detector row 4Z. The γ-ray detection signals output from the first radiation detectors 4 in detector row 4X are conveyed to a γ-ray discriminator 8 via the selector switch 62. The γ-ray detection signals output from the radiation detectors 4 in detector rows 4Y and 4Z are conveyed to the associated γ-ray discriminators 8 via the wiring 13.

In accordance with the input X-ray detection signals, the X-ray signal processors 66 calculate the X-ray detection signal intensity and output it to the computer 11. On the other hand, the γ-ray discriminators 8 use the input γ-ray detection signals to output a pulse signal that corresponds to the γ-ray energy attenuation in the radiation detectors 4 that have generated the γ-ray detection signals. The output pulse signal is conveyed to the coincidence counter 9A.

In accordance with pulse signals that are output from the γ-ray discriminators 8 and entered within a preselected period of time (e.g., within 10 nsec), the coincidence counter 9A identifies the two radiation detectors 4 that output the detection signals for γ-rays unscattered in the radiation detectors 4 (these γ-rays are hereinafter referred to as unscattered γ-rays), and outputs a PET image data signal, which contains the information about the positions of the radiation detectors 4 (initial incidence positions) and the direction of initial incidence, to the computer 11 (the process will be detailed later with reference to FIG. 22). Further, the coincidence counter 9A counts the two pulse signals that are generated due to the γ-ray detection signals entered within the above-mentioned preselected period of time from two identified radiation detectors 4, and outputs the resulting count, data to the computer 11. To remove the detection signals for γ-rays scattered within the body of the medical examinee 17, the coincidence counter 9A checks whether the total energy attenuation for the γ-ray detection signals generating the input pulse signals (total energy) is higher than a predefined energy threshold value (checks whether γ-rays are not scattered within the body of the medical examinee 17). If the total energy is equal to or lower than the threshold energy value, the coincidence counter 9A removes the pulse signal count data based on such γ-ray detection signals. In a nutshell, the initial incidence positions are the positions of two radiation detectors 4 that were the first to detect paired γ-rays emitted from the body of the medical examinee 17.

The computer 11 performs processing steps 90, 91, 71, 72A, 73, and 74 shown in FIG. 20. In step 90, the computer 11 first inputs the γ-ray detection signal count data from the coincidence counter 9A, the positional information about the associated detection points, and the X-ray detection signals from the X-ray signal processors 66. In step 91, the computer 11 stores these items of input information into the storage device 12. In step 71, the computer 11 uses the X-ray detection signal intensity to calculate the rate of X-ray attenuation in each voxel for the body of the medical examinee 17. As is the case with Embodiment 3, the computer 11 also uses the attenuation rate in step 71 to generate X-ray CT image data about cross sections of the medical examinee 17.

In step 72A, the PET image data about cross sections of the medical examinee 17, including a diseased area (e.g., carcinomatous lesion), is generated. Processing steps 41, 42, and 44 through 47 (processing steps shown in FIG. 5 for Embodiment 1), which are performed in step 72 for Embodiment 3, are performed in step 72 A. In Embodiment 6, however, no transmission data imaging is conducted with the calibrated radiation source 31. In step 44, therefore, the in-vivo attenuation correction count (reciprocal of linear attenuation coefficient) is calculated according to the alternative in-vivo absorption correction method described with reference to Embodiment 1 and not in accordance with the γ-ray detection signals obtained during transmission data imaging. In step 73, the PET image data and X-ray CT image data are synthesized to create synthesized tomogram data as is the case with Embodiment 3. The created data appears on the display device 130 (step 74).

It is possible that γ-rays detected by a certain radiation detector 4 may scatter. Generated γ-rays change their traveling direction when they are scattered. If either or both of paired γ-rays detected by the coincidence counter 9A are scattered γ-rays, the straight line joining the radiation detectors 4 that detected such γ-rays does not pass the generation source for the detected γ-rays. To increase the reliability of PET images generated for PET examination, it is therefore necessary to accurately determine whether the obtained γ-ray detection signals relate to scattered γ-rays or unscattered γ-rays, and locate an increased number of radiation detectors 4 that detected unscattered paired γ-rays.

Figure 22:
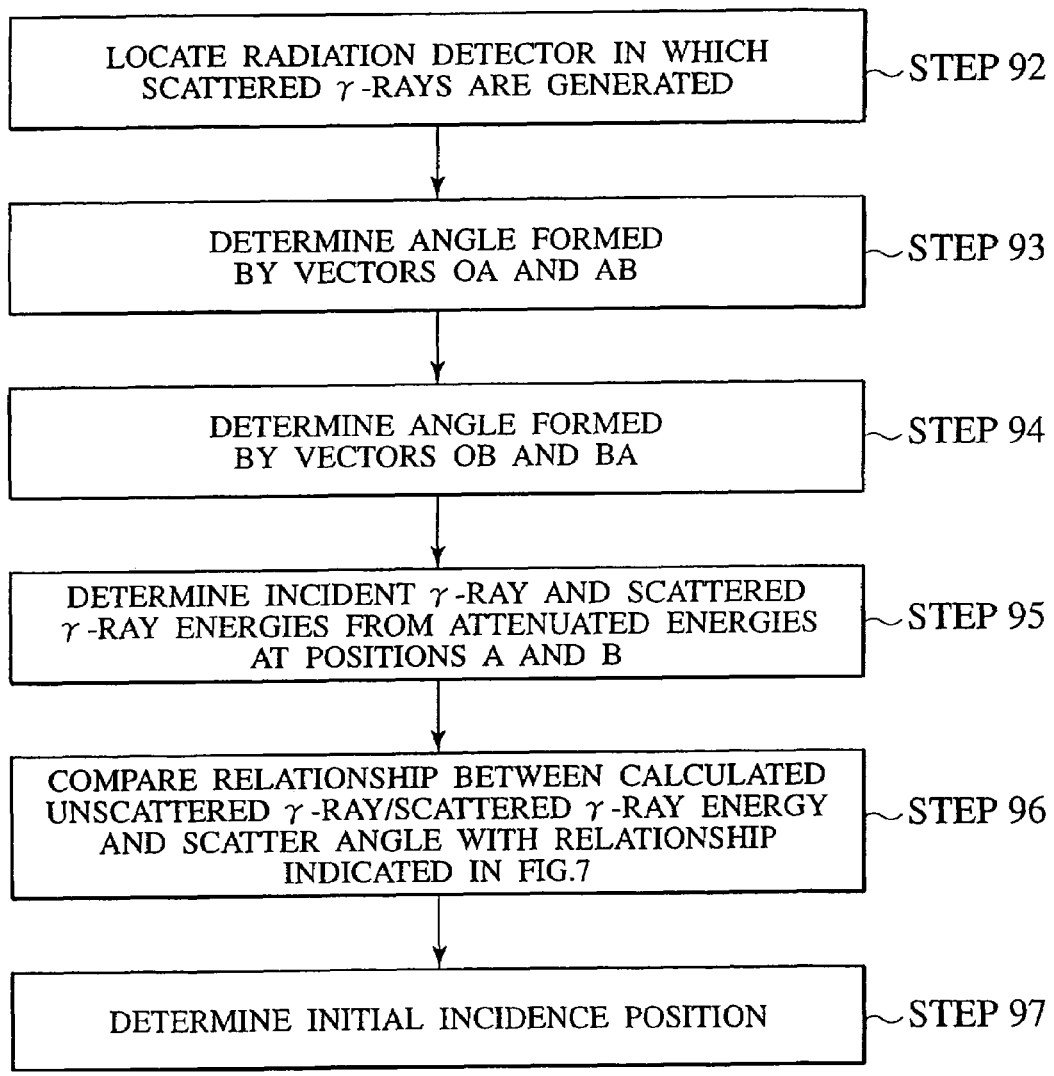
FIG. 22 is a flow chart that illustrates how a coincidence counter shown in FIG. 18 determines the position and direction of γ-ray initial incidence.

A major feature of the radiological imaging apparatus 1C is to determine the positions and directions of paired γ-ray initial incidence by performing the procedure indicated in FIG. 22. In Embodiment 6, two different situations are considered. In one situation, the detection signals (γ-ray image pickup signals) are output by three or more radiation detectors 4 according to the aforementioned coincidence counter 9A during a preselected period of time (e.g., 10 nsec). In the other situation, such detection signals are output by two or fewer radiation detectors 4. A characteristic procedure is a processing procedure for identifying the positions and directions of γ-ray initial incidence in cases where three or more γ-ray image pickup signals are picked up by coincidence counting.

Figure 21:
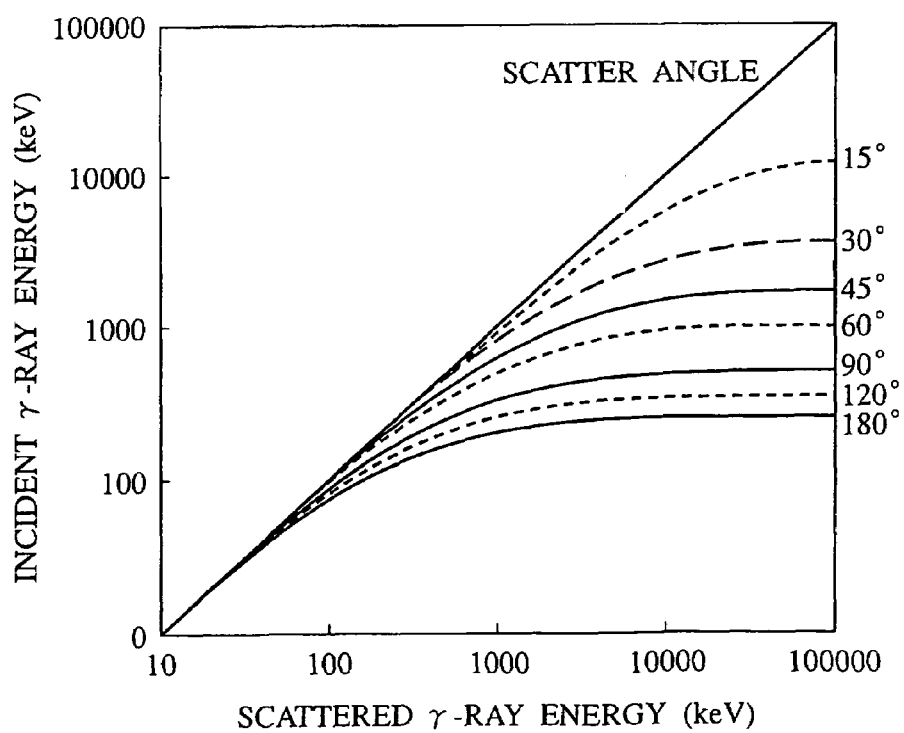
FIG. 21 shows characteristic curves that indicate the γ-ray energy-scatter angle relationship prevailing before and after scattering.

First of all, the processing procedure for determining the positions and directions of γ-ray initial incidence in cases where three or more radiation detectors 4 are picked up by coincidence counting will be described. FIG. 21 shows the energy/scatter angle relationship between unscattered γ-rays incident on a radiation detector 4 and γ-rays scattered within the radiation detector 4. In Embodiment 6, the characteristic shown in FIG. 21 is taken into account. When, for instance, one of a pair of γ-rays is scattered within a radiation detector 4 that achieved γ-ray detection (that is, if three or more γ-rays sharing the same generation source exist, including scattered γ-rays), the radiation detectors 4 that detected unscattered γ-rays (initial incidence positions) and the directions of initial incidence are determined from the scatter angle of scattered γ-radiation while making use of the data about an unscattered γ-ray paired with an unscattered γ-ray serving as a scattered γ-ray generation source. Scattered γ-rays are generated when unscattered γ-rays are scattered within a radiation detector 4 that detected such unscattered γ-rays.

A case where a PET examination is conducted for cancer screening will be described as an example. Under normal conditions, fluoro-deoxyglucose ($^{18}$FDG), which is a form of glucose that tends to gather at cancer cells, is first administered to a medical examinee 17 as a PET pharmaceutical. When administered, $^{18}$FDG emits positrons. When positrons annihilate, a pair of γ-rays having a predefined energy (511 keV when $^{18}$FDG is administered) are emitted. These unscattered paired γ-rays emitted from the same source travel in virtually opposite directions. The energy of unscattered γ-rays incident on a radiation detector 4 remains at 511 keV unless they are scattered within the body of the medical examinee 17 or elsewhere before being incident on the radiation detector 4.

Suppose that, when $^{18}$FDG is uses as a PET pharmaceutical, paired γ-rays having an energy of 511 keV are emitted in this manner from the body of the medical examinee 17, one of the unscattered paired γ-rays suffers 100 keV attenuation in radiation detector 4g shown in FIG. 19, scattered γ-rays generated in radiation detector 4g due to such an unscattered γ-ray suffer 100 keV attenuation in radiation detector 4h, and the remaining unscattered paired γ-ray suffers total attenuation in radiation detector 4f (the positions of radiation detectors 4f, 4g, and 4h are regarded as O, A, and B, respectively). Radiation detectors 4f, 4g, 4h in which γ-rays are attenuated output γ-ray detection signals. In this instance, the paired γ-rays are emitted in opposite directions due to a PET pharmaceutical gathered in a diseased area. Therefore, the direction of paired γ-ray travel (more specifically the traveling direction of an opposite unscattered γ-ray) is a combination of the vector OA and vector AO or a combination of the vector OB and vector BO. If the direction of an unscattered γ-ray is the vector OA (the initial incidence position is position A), the energy of a scattered γ-ray is 411 keV. If the direction of an unscattered γ-ray is the vector OB (the initial incidence position is position B), the energy of a scattered γ-ray is 100 keV. In other words, when the initial incidence position of an unscattered γ-ray is position A, the direction of a scattered γ-ray is the vector AB. If the initial incidence position is position B, the direction of a scattered γ-ray is the vector BA. The unscattered γ-ray energy is equal to the sum of both energy attenuations, that is 411+100=511 keV, no matter whether initial incidence occurs at position A or position B. The above energy attenuation values depend on the pulse height of a pulse signal output from a γ-ray discriminator 8. It can therefore be said that the energy attenuation values are detected by the associated γ-ray discriminators 8.

In Embodiment 6, the coincidence counter 9A performs processing steps 92 through 97 shown in FIG. 22 to determine the positions and directions of γ-ray initial incidence, using the energy attenuation values detected in relation to the above γ-rays and the positional information about radiation detectors 4 on which such γ-rays are incident. The positional information about radiation detectors 4 that output γ-ray detection signals is converted to a pulse signal by the γ-ray discriminators 8 provided for the radiation detectors 4 and conveyed to the coincidence counter 9A. In step 92, the coincidence counter 9A first determines a radiation detector candidate that generated a scattered γ-ray. When three or more pulse signals are entered during the aforementioned preselected period of time, the coincidence counter 9A checks three or more radiation detectors 4 that output γ-ray detection signals, which have caused the generation of the pulse signals, and then determines a radiation detector that has generated a scattered γ-ray. This determination is made in accordance with the distance between the associated radiation detectors 4. In other words, radiation detectors 4 positioned at a spacing interval shorter than preselected are the radiation detectors 4 that have generated scattered γ-rays. Since the scattered γ-ray transmission distance is short, suppose that the distance setting is 5 cm. In the example shown in FIG. 19, in which γ-ray detection signals are output within a preselected period of time by radiation detectors 4f, 4g, and 4h, if the distance between the radiation detectors 4g and 4h is 5 cm or shorter, scattered γ-rays are generated by either the radiation detector 4g or the radiation detector 4h. The radiation detectors 4g and 4h are determined as radiation detector candidates that have generated scattered γ-rays. Therefore, the coincidence counter 9A recognizes that an unscattered γ-ray is detected by the remaining radiation detector 4f.

In step 93, which is performed after the radiation detectors 4g and 4h are designated as radiation detector candidates that have generated scattered γ-rays, the scatter angle (angle formed by the vectors OA and AB) prevailing when the radiation detector 4g, that is, position A is the initial incidence position is calculated. In step 94, the scatter angle (angle formed by the vectors OB and BA) prevailing when radiation detector 4h, that is, position B is the initial incidence position is calculated. In this instance, the angle θ, which is formed by the vectors OA and AB, can be calculated as indicated below:

$$\theta = \cos^{-1}\left(\vec{OA} \cdot \vec{AB}\right) / \left(\left|\vec{OA}\right| \cdot \left|\vec{AB}\right|\right) \quad (3)$$

The next step, which is step 95, is performed to calculate the unscattered γ-ray incidence energy and scattered γ-ray energy. More specifically, the coincidence counter 9 calculates the γ-ray energy attenuations in the radiation detectors 4g and 4h in accordance with the pulse heights of pulse signals generated due to individual γ-ray detection signal outputs from the radiation detectors. The energy attenuation of a γ-ray incident on radiation detector 4f in the initial incidence position is calculated to be 511 keV according to the pulse height of the associated pulse signal. Further, the energy attenuation of a γ-ray incident on the radiation detector 4g is calculated to be 100 keV according to the pulse height of the associated pulse signal. In like manner, the energy attenuation of a γ-ray incident on radiation detector 4h is calculated to be 411 keV. A scattered γ-ray is generated by the radiation detector 4g or 4h. An unscattered γ-ray is detected by the radiation detector 4g or 4h, whichever did not generate the scattered γ-ray. The energy of unscattered γ-ray incidence is the sum of energy attenuations in the radiation detectors 4g and 4h and calculated to be 511 keV.

Next, the scattered γ-ray energy is calculated on the presumption that scattered γ-rays are generated in both of the radiation detectors 4g and 4h. When a scattered γ-ray is generated in the radiation detector 4g, the energy of that scattered γ-ray is 411 keV (=511 keV −100 keV). In this instance, the scattered γ-ray eventually attenuates in the radiation detector 4h. When a scattered γ-ray is generated in the radiation detector 4h, the energy of that scattered γ-ray is 100 keV (=511 keV −411 keV). In this instance, the scattered γ-ray eventually attenuates in the radiation detector 4f. If, for instance, the calculated energy of an unscattered γ-ray is considerably lower than 511 keV (e.g., below 350 keV), such a ray is excluded because it is conceivable that it was previously scattered within the body of the medical examinee 17.

When the initial incidence position is either position A or position B, steps 93 through 95 are performed to calculate the incident γ-ray energy, scattered γ-ray, energy, and scatter angle. Step 96 is performed to determine what attenuation sequence (scattering sequence) is appropriate by checking whether the calculated relationship among incidence γ-ray energy, scattered γ-ray energy, and scatter angle agrees with the relationship indicated in FIG. 21. If, for instance, a scatter angle comparison is to be made, the incident γ-ray energy and scattered γ-ray energy indicated in FIG. 21 are used to calculate an ideal scatter angle and determine the deviation of the actual scatter angle from the ideal one. An appropriate threshold value (e.g., for tolerating a deviation of up to 10%) is set for the relationship between calculation results and FIG. 21. When the threshold value is not exceeded by the deviation, it is concluded that an expected phenomenon can occur (the attenuation sequence is proper). When it is concluded that one of two or more phenomena (two phenomena in the currently used example) can occur, such a phenomenon is selected. (Cases where it is concluded that two or more phenomena can occur will be explained later.) As a result, the initial incidence positions of paired γ-rays are determined. Finally, step 91 is performed to output a PET image data signal, which contains the information about the initial incidence positions of unscattered paired γ-rays and the straight line (direction of initial incidence) joining these positions, to the computer 11. The procedure is now completed.

As described earlier, the computer 11 stores a large number of PET image data, which is entered in the above manner, into the storage device 12, reconstructs them to formulate a PET image, and displays it on the display device 130.

If it concluded after the above procedure is performed in cases where three or more detection signals are counted that the initial incidence position can be either position A or position B, an alternative is to remove the associated γ-ray detection signals or select an attenuation sequence so as to minimize the deviation from the relationship indicated in FIG. 21. In the above-described situation, one of paired γ-rays is attenuated (subjected to two attenuations) by two radiation detectors 4 (this example is simple because either of two different attenuation sequences is to be selected). However, it is also possible to determine a proper attenuation sequence by performing the above-described procedure for all possible patterns, including the one in which generated paired γ-rays are both scattered a number of times within the radiation detectors 4. Another alternative is to define the positional relationship between the radiation detectors 4 that cannot physically be subjected to coincidence counting due to the layout of the radiation detectors 4, and remove a pulse signal that corresponds to the defined positional relationship.

Meanwhile, if two γ-ray detection signals are simultaneously counted, the coincidence counter 9A concludes that they relate to paired γ-rays, and outputs the positional information about radiation detectors 4 that detected such rays and the PET image data including the information about the direction of a straight line joining such radiation detectors to the computer 11. Alternatively, a different configuration may be used to achieve γ-ray detection signal removal when only one γ-ray detection signal is counted. In another alternative configuration, a data signal containing the information about the direction of a straight line joining the radiation detector 4 that achieved γ-ray detection to an opposing radiation detector, which is positioned 180° apart, may be output to the computer 11 in a manner similar to a conventional one.

Embodiment 6 provides the following advantages in addition to advantages (1) through (13) of Embodiment 3.

(14) PET image accuracy enhancement

Embodiment 6 makes it possible to effectively determine the positions and directions of paired γ-ray initial incidence by performing a predetermined procedure indicated in FIG. 22. As a result, highly reliable data can be output to the computer 11 to enhance the PET image accuracy. Although $^{18}$FDG is used as a PET pharmaceutical for the explanation of Embodiment 6, the aforementioned processing procedure for determining the positions and directions of γ-ray initial incidence is also applicable to cases where the employed PET pharmaceutical contains the other radionuclides.

(15) PET image accuracy enhancement

In Embodiment 6, the positional information about radiation detectors that have detected a γ-ray and the positional information about radiation detectors that have detected the other γ-ray are used to set up possible attenuation sequences of the former γ-ray. These γ-ray attenuation sequences are examined to select an appropriate one, which exhibits a proper relationship between the γ-ray scatter angle and energy detection value. In this manner, the γ-ray attenuation sequence is determined. As a result, the position of initial γ-ray incidence on a radiation detector is determined. It can therefore be concluded that a γ-ray generation source (diseased area) exists on a straight line (direction of initial incidence) joining the determined radiation detector to a radiation detector that detected the other γ-ray. Unlike probabilistic determination of initial γ-ray incidence position, unscattered γ-rays can be determined with high efficiency to generate a highly accurate PET image.

In particular, when the γ-ray detection signals of three or more radiation detectors are simultaneously counted, Embodiment 6 uses the positional information about the three or more γ-ray detection signals to set up possible γ-ray attenuation sequences, and selects an appropriate sequence that exhibits a proper relationship to energy detection values from the three or more radiation detectors. The initial γ-ray incidence position determined in this manner and the above energy detection value data can then be used to determine the direction of initial γ-ray incidence. Unlike probabilistic determination of initial γ-ray incidence position, unscattered γ-rays can be determined with high efficiency to generate a highly accurate PET image.

(16) Incorporation of X-ray CT examination and PET examination functions

In the past, an image pickup device for detecting transmitted X-rays was generally installed independently of an image pickup device for detecting γ-rays. However, Embodiment 6 uses the same radiation detectors 4 to detect X-rays and γ-rays. Therefore, the aforementioned image pickup device 2 can provide both X-ray CT examination and PET examination although it has a simple, compact structure.

Embodiment 7

Figure 23:
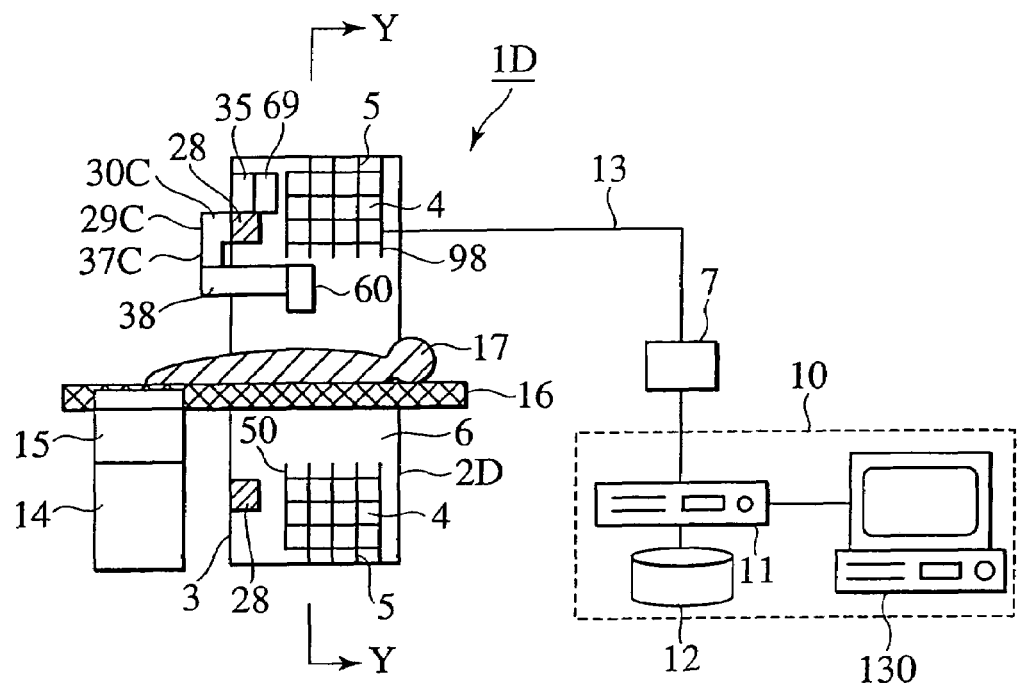
FIG. 23 is a configuration diagram showing a radiological imaging apparatus according to another embodiment of the present invention.

A radiological imaging apparatus of another embodiment (Embodiment 7) of the present invention will be described with reference to FIGS. 23 and 24. The radiological imaging apparatus 1D of Embodiment 7 is a two-dimensional measurement type radiological imaging apparatus. Embodiment 7 determines the γ-ray attenuation sequence from the energies and scatter angles of unscattered γ-rays and scattered γ-rays, and provides a detection efficiency improvement over single γ-ray detection by a two-dimensional measurement type radiological imaging apparatus. In two-dimensional measurements, the apparatus uses a collimator to remove γ-rays that are initially incident at a certain angle on the direction of the radiation detector body axis (equivalent to the axial direction of the aforementioned through-hole 6), and detects only γ-rays that are initially incident perpendicularly to the direction of the body axis. Two-dimensional measurements, in which γ-rays incident at a certain angle are removed, generally decrease the γ-ray pair count per unit time, but offer an advantage that the influence of scattered γ-rays can be minimized.

The radiological imaging apparatus 1D has the same configuration as the radiological imaging apparatus 1C, except that an image pickup device 2D of the radiological imaging apparatus 1d includes a collimator 98. The collimator 98 is mounted on a detector support plate 5 and positioned in front of (inner circular side of) radiation detectors 4 in the innermost detector row 4X (see FIG. 18).

For PET examination, X-ray CT examination, and synthesized tomogram data creation, the radiological imaging apparatus 1D uses the procedures as the radiological imaging apparatus 1C. However, the process performed by the radiological imaging apparatus 1D for determining the positions and directions of initial γ-ray incidence is different from that which is performed by the radiological imaging apparatus 1C. Embodiment 7 determines the γ-ray attenuation sequence when γ-rays incident radiation detectors 4 after passing through the collimator 98 are scattered three or more times within a radiation detector 4. For the sake of brevity, Embodiment 7 is described here on the presumption that γ-rays incident on radiation detectors 4 totally attenuate in radiation detectors 4i, 4j, and 4k in an arbitrary order as indicated in FIG. 24. However, the positions of the radiation detectors 4i, 4j, and 4k are regarded as positions A, B, and C, respectively, and the energies attenuated at positions A, B, and C are regarded as $E_A$, $E_B$, and $E_C$, respectively. For the sake of convenience, the drawings depicting Embodiment 7 are prepared on the presumption that positions A, B, and C are in the same plane. However, the following description of Embodiment 7 is also applicable to cases where positions A, B, and C are not in the same plane as indicated in FIG. 24.

Figure 24:
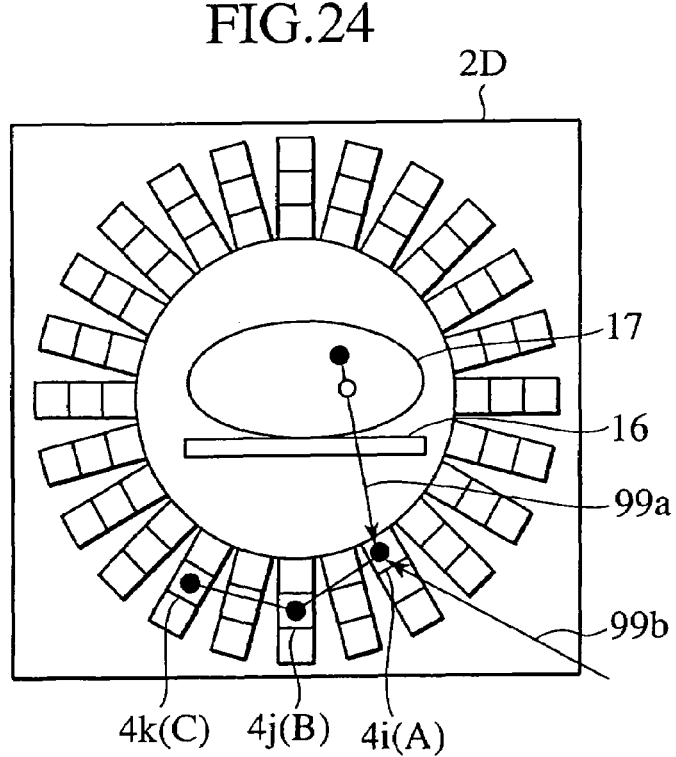
FIG. 24 is a cross sectional view taken along line Y-Y of FIG. 23.

From FIG. 24, six different attenuation sequences are conceivable: ① B→A→C, ② C→A→B, ③ A→B→C, ④ C→B→A, ⑤ A→C→B, and ⑥ B→C→A. Further, since total attenuation occurs at positions A, B, and C, the γ-ray energy prevailing at the time of initial incidence (total energy E) is $E_A+E_B+E_C$. Therefore, the energy of scattered γ-ray incident on the second attenuation position is determined by subtracting the first energy attenuation ($E_A$, $E_B$, or $E_C$) from the total energy E. The energy of the γ-ray scattered at the second position is the energy of scattered γ-ray incident on the third attenuation position ($E_A$, $E_B$, or $E_C$).

Therefore, the scattered γ-ray scatter angel at the second attenuation position and the incoming energy and outgoing energy as viewed from the second attenuation position are calculated with respect the above-mentioned six different attenuation sequences. The obtained results are then compared with the relationship indicated in FIG. 7 to check the six different attenuation sequences to determine a proper attenuation sequence that can occur in reality.

Next, the scatter angle at the initial incidence position is determined in accordance with the attenuation sequence determined in this manner. If, for instance, the attenuation sequence ③ (A→B→C) is found to be proper as a result of the check of the six different attenuation sequences, the incidence energy prevailing at the first attenuation position A is $E_A+E_B+E_C$, and the outgoing energy is $E_B+E_C$. When these energy values compared with the relationship indicated in FIG. 21, the scatter angle prevailing at position A is identified. When considering the fact that only γ-rays perpendicular to the direction of the body axis are incident on the radiation detectors 4 in a two-dimensional measurement PET examination, it is concluded that the direction of initial γ-ray incidence is indicated by arrow 99a or 99b in FIG. 24. As is obvious from FIG. 24, the existence range of a γ-ray generation source does not physically allow the arrow 99b to represent the direction of initial γ-ray incidence. Therefore, it is uniquely concluded that the γ-rays are initially incident on the radiation detector 4g (initial incidence position) and that the initial incidence direction is as indicated by the arrow 99a.

If no more than two γ-ray detection signals were simultaneously counted (that is, if the attenuation in radiation detectors did not occur more than two times), the associated data is removed and not used. An alternative is to determine the first attenuation position on the presumption that uniform incidence occurs from the range of radiation source existence.

Embodiment 7 uses a coincidence counter 9A to determine the positions and directions of initial γ-ray incidence. As described earlier, a γ-ray discriminator 8 converts a γ-ray detection signal having an energy value not less than a predefined threshold value to a pulse signal, and outputs it to the coincidence counter 9A. In this instance, not only the pulse signal but also the positional information about a radiation detector 4 whose γ-ray detection signal is detected is output to the coincidence counter 9A. The coincidence counter 9A determines the position and direction of γ-ray initial incidence in accordance with the pulse signal input from the γ-ray discriminator 8, and outputs a PET image data signal, which contains the information about the position and direction of γ-ray initial incidence, to the computer 11. When three or more pulse signals are simultaneously counted, Embodiment 7 causes the coincidence counter 9A to perform the above procedure for determining the position and direction of initial incidence. In the other situations, however, the coincidence counter 9A performs the following procedures depending on the encountered situation.

FIG. 25 shows typical input and output signals of the coincidence counter 9A. The numbers parenthesized in FIG. 25 indicate the number of signal inputs or outputs. If, for instance, the position and direction of γ-ray initial incidence are determined from an input pulse signal as in a case i, v, or vi shown in FIG. 25, the coincidence counter 9A outputs a PET image data signal, which contains the information about the determined position and direction of initial incidence, to the computer 11. If, for instance, there is no pulse signal input (case i), one totally-attenuated γ-ray pulse signal is entered (case ii), or three pulse signals, which cannot possibly be generated from the same source due to the layout of radiation detectors 4, are counted (case vii), the coincidence counter 9A remove the pulse signal(s) and does not output a PET image data signal. If two totally-attenuated γ-ray pulse signals are counted (case iv), the coincidence counter 9A outputs a data signal, which contains the positional information about radiation detectors 4 whose signals are detected and a straight line joining these radiation detectors, to the computer 11.

As is the case with Embodiment 6, the computer 11 stores the input PET image data signal in the storage device 12. The count data for the aforementioned γ-ray detection signals are also stored into the storage device 12 by the computer 11. If three or more signals are counted (case vii) and the direction of incidence is known, the data for that direction may be output. The data obtained in this manner is reconstructed by the computer 11 and displayed on the display device 130.

Embodiment 7 provides some advantages in addition to the advantages of Embodiment 6. When either or both of paired γ-rays are scattered, Embodiment 6 determines the attenuation sequence of a targeted unscattered γ-ray in accordance with the detection signal for the remaining unscattered γ-ray. However, Embodiment 7 can consider the scatter status of a paired γ-ray and determine the initial incidence position and direction (that is, initial incidence direction) of an unscattered γ-ray during a two-dimensional measurement PET examination even when the remaining paired γ-ray is totally attenuated (absorbed) within the body of a medical examinee. In this manner, Embodiment 7 can collect the data about unscattered γ-rays with high efficiency and increase the PET image accuracy. As a result, the count per unit time of two-dimensional measurement PET examination increases, making it possible to reduce the examination time. It can also be expected that this advantage will reduce the load on a medical examinee 17 and increase the throughput of the number of medical examinees. If the incidence of each of paired γ-rays is verified, the scattered γ-ray attenuation sequence determination procedure performed for Embodiment 6 is also applicable to a two-dimensional measurement type PET examination apparatus described according to Embodiment 7.

In an X-ray CT image creation example that is described according to Embodiments 6 and 7, the arm 38 is sequentially extended and contracted to create tomograms of various cross sections of a medical examinee 17. However, when the X-ray source 60 is rotated simultaneously with the extension/contraction of the arm 38, Embodiments 6 and 7 are applicable to an X-ray helical scan as well. Further, an alternative configuration may be employed so that the bed 16 moves in the axial direction of the through-hole 6 instead of the extension/contraction of the arm 38.

The above PET/X-ray examination procedure may be performed in relation to the entire body of a medical examinee 17 or in relation to the neighborhood of the medical examinee's diseased area roughly located beforehand by another examination. In some situations, the examination may be conducted without administering a PET pharmaceutical to the medical examinee 17 in advance but administering the PET pharmaceutical to the medical examinee 17 laid on the bed 16, or conducted while administering the PET pharmaceutical to the medical examinee 17. An alternative configuration, which is not specifically described with reference to the above first and second embodiments, may be employed so that the radiological imaging apparatus 1C, 1D is provided with a separate calibrated radiation source to perform transmission imaging. These alternative embodiments also provide the same advantages.

In Embodiments 6 and 7, a predetermined procedure is followed so that the coincidence counter 9A determines the γ-ray attenuation sequence, initial incidence position, and initial incidence direction. Alternatively, however, a separate circuit performing this process may be furnished to complete the process at high speed. Another alternative scheme may be used so that a coincidence counter circuit merely selects simultaneous events, allowing the software to carry out the subsequent processing steps. That is, when, for instance, three signals are entered, the coincidence counter 9A sends information, which contains the data for indicating that the three signals are coincident, to the computer 11, and the computer 11 performs a predetermined procedure to determine the attenuation sequence, initial incidence position, and initial incidence direction. Even if each radiation detector is provided with a storage area, the γ-ray incidence time and the γ-ray energy attenuation in a radiation detector are written in such an area, and the computer 11 reads the written data to check for coincidence, the computer 11 can determine the attenuation sequence, initial incidence position, and initial incidence direction by performing a predetermined procedure. In this instance, also the same advantages are obtained.

In Embodiments 6 and 7, the incidence scatter angle can be determined even if one of paired γ-ray is scattered in a radiation detector and the remaining paired γ-ray is not detected by a radiation detector. If it is known that the γ-rays are emitted from a certain area (e.g., from within a plane), the above property can be used to determine which of the areas into which the γ-rays can enter is the source of generation. These data can be effectively used to raise the detection efficiency of radiation detectors and reduce the load on patients.

In Embodiments 6 and 7, the radiation detectors 4 in multiple layers are linearly arranged in the radial direction with the innermost ones regarded as the base points as shown in FIGS. 19 and 24. Alternatively, however, the radiation detectors 4 may be zigzagged in the direction of the radius. Although the above descriptions deal with a PET examination in which emitted paired γ-rays are to be detected, it is also possible that α- and γ-rays or β- and γ-rays may be paired when emitted. In these instances, the above-described attenuation sequence determination procedure works because γ-rays may scatter multiple times although the α- and β-rays have a low penetrating power. Although the above descriptions deal with cases where the coincidence counter 9A determines the positions of γ-ray initial incidence, it is alternatively possible that the position, energy detection value, and detection time data about the radiation detectors 4 may be output to the computer 11 to allow the computer 11 to perform the above-described processing procedure. In all the above cases, also the same advantages are obtained.

What is claimed is:

1. A radiological imaging apparatus comprising:
   a bed for laying a subject thereon;
   an image pickup device, comprising:
      a plurality of radiation detectors for detecting a plurality of radiations from said subject, wherein one certain radiation passed through a first radiation detector of said radiation detectors is detected by a second radiation detector of said radiation detectors; and
      an X-ray source for moving around said subject and irradiating X-rays to said subject,
      wherein said first and second radiation detectors are arranged in a plurality of layers in a direction away from said bed around said bed, wherein said first radiation detector which is the first layer from a bed side outputs a first detection signal of an X-ray passed through said subject, said X-ray being one of said certain radiation and a second detection signal of a γ-ray emitted from said subject, said γ-ray being another of said certain radiation; and
      a signal processing apparatus connected to said plurality of radiation detectors, for processing radiation detection signals detected by said radiation detectors.

2. The radiological imaging apparatus according to claim 1 wherein said image pickup device comprises a γ-ray source for moving around said subject and irradiating γ-rays to said subject, and said radiation detectors output a third detection signal of a γ-ray passed through said subject after irradiation from said γ-ray source.

3. The radiological imaging apparatus according to claim 1 further comprising a controller for controlling irradiation of X-rays from said X-ray source in a manner that irradiation and stop of irradiation of said X-rays are performed alternately, and that said irradiation of said X-rays is performed during a set period of time.

4. The radiological imaging apparatus according to claim 1 further comprising a tomographic image data creating apparatus for creating a synthesized tomographic image data by synthesizing a first tomographic image data and a second tomographic image data, said first tomographic image data of said subject being created on the basis of first information output from said signal processing apparatus due to input of said first detection signal, and said second tomographic image data of said subject being created on the basis of second information output from said processing apparatus due to input of said second detection signal.

5. The radiological imaging apparatus according to claim 2, further comprising a tomographic image data creating apparatus for creating a synthesized tomographic image data by synthesizing a first tomographic image data and a second tomographic image data, said first tomographic image data of said subject being created on the basis of first information output from said signal processing apparatus due to input of said first detection signal, and said second tomographic image data of said subject being created on the basis of corrected second information obtained by correcting second information output from said processing apparatus due to input of said second detection signal on the basis of third information output from said signal processing apparatus due to input of said third detection signal.

6. The radiological imaging apparatus according to claim 1, further comprising a tomographic image data creating apparatus,
   wherein said signal processing apparatus connected to said first radiation detector comprises an X-ray signal processing apparatus for outputting first information concerning X-rays on the basis of said first detection signal and a γ-ray signal processing apparatus for outputting second information concerning γ-rays on the basis of said second detection signal, and
   wherein said signal processing apparatus connected to said second radiation detector comprises said γ-ray signal processing apparatus and does not comprise said X-ray signal processing apparatus,
   wherein said tomographic image data creating apparatus creates a first tomographic image data of said subject on the basis of said first information output from said X-ray signal processing apparatus and a second tomographic image data of said subject on the basis of said second information output from said γ-ray signal processing apparatus and a synthesized tomographic image data obtained by synthesizing said first tomographic image data and said second tomographic image data.

7. The radiological imaging apparatus according to claim 2, further comprising a tomographic image data creating apparatus,
   wherein said signal processing apparatus connected to said first radiation detector comprises an X-ray signal processing apparatus for outputting first information concerning X-rays on the basis of said first detection signal and a γ-ray signal processing apparatus for outputting second information concerning γ-rays on the basis of said second detection signal and third information concerning γ-rays on the basis of said third detection signal, and
   wherein said signal processing apparatus connected to said second radiation detector comprises said γ-ray signal processing apparatus and does not comprise said X-ray signal processing apparatus,
   wherein said tomographic image data creating apparatus creates a first tomographic image data of said subject on the basis of said first information output from said X-ray signal processing apparatus and corrects second information output from said γ-ray signal processing apparatus on the basis of third information output from said signal processing apparatus and creates a second tomographic image data on the basis of said second information corrected and creates a synthesized tomographic image data obtained by synthesizing said first tomographic image data and said second tomographic image data.

8. The radiological imaging apparatus according to claim 1 wherein said radiation detectors in the second layer from said bed side are not linearly arranged in a direction toward said bed with respect to said radiation detectors in the first layer from said bed side, but arranged to as to face an intermediate portion between said plurality of radiation detectors in the first layer.

9. The radiological imaging apparatus according to claim 1 wherein said radiation detectors in the second layer from said bed side are not linearly arranged in a direction toward said bed with respect to said radiation detectors in the first layer from said bed side, but arranged so as to overlap with two of said radiation detectors in the first layer.

10. A radiological imaging apparatus comprising:

a bed for laying a subject thereon;

an image pickup device comprising a plurality of radiation detectors arranged in a plurality of layers in a direction away from said bed around said bed; and a signal processing apparatus connected to said plurality of radiation detectors, for processing radiation detection signals detected by said radiation detectors, wherein said radiation detectors in the second layer from a bed side are not linearly arranged in a direction toward said bed with respect to said radiation detectors in the first layer from said bed side, but arranged so as to face an intermediate portion between said plurality of radiation detectors in the first layer.

11. A radiological imaging apparatus comprising:

a bed for laying a subject thereon;

an image pickup device comprising a plurality of radiation detectors arranged in a plurality of layers in a direction away from said bed around said bed; and a signal processing apparatus connected to said plurality of radiation detectors, for processing radiation detection signals detected by said radiation detectors, wherein said radiation detectors in the second layer from a bed side are not linearly arranged in a direction toward said bed with respect to said radiation detectors in the first layer from said bed side, but arranged so as to overlap with two of said plurality of radiation detectors in the first layer.

* * * * *